(12) United States Patent
Deppermann et al.

(10) Patent No.: US 10,705,102 B2
(45) Date of Patent: *Jul. 7, 2020

(54) AUTOMATED SYSTEMS FOR REMOVING TISSUE SAMPLES FROM SEEDS, AND RELATED METHODS

(71) Applicant: Monsanto Technology LLC, St. Louis, MO (US)

(72) Inventors: Kevin L. Deppermann, St. Charles, MO (US); Michael W. Petersen, Sauk City, WI (US); Allen N. Ondes, Troy, MO (US); David W. Finley, Crestwood, MO (US); William M. Fischer, St. Peters, MO (US); John M. Jensen, Glen Carbon, IL (US); David Butruille, Des Moines, IA (US); Stanton Dotson, Roseville, CA (US); Sam Eathington, Ames, IA (US); Heather M. Forbes, St. Charles, MO (US); Bruce Schnicker, Wildwood, MO (US); John Tamulonis, Nevada, IA (US)

(73) Assignee: Monsanto Technology LLC, St. Louis, MO (US)

( * ) Notice: Subject to any disclaimer, the term of this patent is extended or adjusted under 35 U.S.C. 154(b) by 579 days.

This patent is subject to a terminal disclaimer.

(21) Appl. No.: 14/685,047

(22) Filed: Apr. 13, 2015

(65) Prior Publication Data

US 2015/0355205 A1 Dec. 10, 2015

Related U.S. Application Data

(63) Continuation of application No. 13/186,126, filed on Jul. 19, 2011, now Pat. No. 9,003,696.

(Continued)

(51) Int. Cl.
*A01C 1/00* (2006.01)
*G01N 35/00* (2006.01)
(Continued)

(52) U.S. Cl.
CPC ....... *G01N 35/00584* (2013.01); *A01C 1/025* (2013.01); *G01N 1/04* (2013.01);
(Continued)

(58) Field of Classification Search
CPC ............ A01C 1/025; A01C 1/00; G01N 1/00
See application file for complete search history.

(56) References Cited

U.S. PATENT DOCUMENTS 3,852,914 A 12/1974 Levengood
4,278,183 A 7/1981 Billington
(Continued)

FOREIGN PATENT DOCUMENTS

CL 1035-03 5/2003
CL 673-03 2/2004
(Continued)

OTHER PUBLICATIONS

Anklam et al., Analytical methods for detection and determination of genetically modified organisms in agricultural crops and plant-derived food products. (Eur Food Res Technol. 214:3-26), Jan. 2002, 24 pages.

(Continued)

*Primary Examiner* — Thanh Pham
(74) *Attorney, Agent, or Firm* — James E. Davis; Harness, Dickey & Pierce, P.L.C.

(57) ABSTRACT

A seed sampling system is provided having an automated seed loading assembly including a seed bin and being operable to singulate seeds from a plurality of seeds within the seed bin. The system also includes an automated seed sampling assembly operable to remove tissue samples from (Continued)

the singulated seeds, and an automated seed transport assembly operable to transfer the singulated seeds from the seed loading assembly to the seed sampling assembly. The seed transport assembly includes multiple retention members. Each of the retention members is movable relative to the seed loading assembly and to the seed sampling assembly. The seed transport assembly is operable to position one of the multiple retention members adjacent to the seed loading assembly for engaging one of the singulated seeds, while positioning another of the retention members adjacent to the seed sampling assembly for presenting another of the singulated seeds to the seed sampling assembly.

17 Claims, 16 Drawing Sheets

Related U.S. Application Data

(60) Provisional application No. 61/365,826, filed on Jul. 20, 2010.

(51) Int. Cl.
G01N 33/00 (2006.01)
G01N 33/50 (2006.01)
G01N 1/20 (2006.01)
G01N 1/28 (2006.01)
A01C 1/02 (2006.01)
G01N 1/04 (2006.01)
G01N 1/00 (2006.01)

(52) U.S. Cl.
CPC .............. *G01N 1/20* (2013.01); *G01N 1/286* (2013.01); *G01N 33/0098* (2013.01); *G01N 33/5097* (2013.01); *A01C 1/00* (2013.01); *G01N 2001/002* (2013.01)

(56) References Cited

U.S. PATENT DOCUMENTS

| 4,305,130 | A | 12/1981 | Kelley |
|---|---|---|---|
| 4,696,308 | A | 9/1987 | Meller et al. |
| 4,827,776 | A | 5/1989 | Gale et al. |
| 5,437,697 | A | 8/1995 | Sebastian et al. |
| 5,677,474 | A | 10/1997 | Rogers |
| 5,746,023 | A | 5/1998 | Hanafey et al. |
| 5,917,927 | A | 6/1999 | Satake et al. |
| 6,307,123 | B1 | 10/2001 | Kriz et al. |
| 6,537,826 | B1 | 3/2003 | Horigane |
| 6,646,264 | B1 | 11/2003 | Modiano et al. |
| 6,809,819 | B1 | 10/2004 | Vinjamoori et al. |
| 6,947,144 | B2 | 9/2005 | Kim et al. |
| 7,044,306 | B2 | 5/2006 | Deppermann |
| 7,067,834 | B2 | 6/2006 | Horigane et al. |
| 7,367,155 | B2 | 5/2008 | Kotyk et al. |
| 7,502,113 | B2 | 3/2009 | Deppermann et al. |
| 7,591,101 | B2 | 9/2009 | Deppermann |
| 7,611,842 | B2 | 11/2009 | Deppermann et al. |
| 7,703,238 | B2 | 4/2010 | Deppermann et al. |
| 7,735,626 | B2 | 6/2010 | Cope et al. |
| 7,767,883 | B2 | 8/2010 | Deppermann et al. |
| 7,830,516 | B2 | 11/2010 | Deppermann et al. |
| 7,832,143 | B2 | 11/2010 | Deppermann et al. |
| 7,849,632 | B2 | 12/2010 | Deppermann et al. |
| 7,877,926 | B2 | 2/2011 | Deppermann et al. |
| 7,915,006 | B2 | 3/2011 | Cope et al. |
| 7,941,969 | B2 | 5/2011 | Deppermann et al. |
| 7,998,669 | B2 | 8/2011 | Deppermann et al. |
| 8,028,469 | B2 | 10/2011 | Deppermann et al. |
| 8,071,845 | B2 | 12/2011 | Deppermann et al. |
| 8,189,901 | B2 | 5/2012 | Modiano et al. |
| 8,245,439 | B2 | 8/2012 | Deppermann et al. |
| 8,312,672 | B2 | 11/2012 | Deppermann et al. |
| 8,434,259 | B2 | 5/2013 | Deppermann et al. |
| 8,436,225 | B2 | 5/2013 | Deppermann et al. |
| 8,443,545 | B2 | 5/2013 | Deppermann et al. |
| 8,501,480 | B2 | 8/2013 | Deppermann et al. |
| 8,539,713 | B2 | 9/2013 | Deppermann et al. |
| 8,561,346 | B2 | 10/2013 | Deppermann et al. |
| 8,959,833 | B2 | 2/2015 | Deppermann et al. |
| 8,997,398 | B2 | 4/2015 | Deppermann et al. |
| 9,003,696 | B2 | 4/2015 | Deppermann et al. |
| 9,027,278 | B2 | 5/2015 | Deppermann et al. |
| 9,383,291 | B2 | 7/2016 | Deppermann et al. |
| 9,448,141 | B2 | 9/2016 | Deppermann |
| 9,551,636 | B2 | 1/2017 | Deppermann et al. |
| 9,986,699 | B2 | 6/2018 | Deppermann et al. |
| 10,132,725 | B2 | 11/2018 | Deppermann |
| 2001/0024796 | A1 | 9/2001 | Selifonov et al. |
| 2002/0070150 | A1 | 6/2002 | Keller et al. |
| 2002/0144458 | A1 | 10/2002 | Hunter et al. |
| 2003/0148273 | A1 | 8/2003 | Kim et al. |
| 2003/0188998 | A1 | 10/2003 | Deppermann |
| 2004/0074822 | A1 | 4/2004 | Horigane et al. |
| 2004/0091888 | A1 | 5/2004 | Nishio et al. |
| 2004/0221335 | A1 | 11/2004 | Shewmaker et al. |
| 2005/0082207 | A1 | 4/2005 | Deppermann |
| 2005/0154221 | A1 | 7/2005 | Lysenko et al. |
| 2006/0046244 | A1 | 2/2006 | Deppermann |
| 2006/0042527 | A1 | 3/2006 | Deppermann |
| 2006/0042528 | A1 | 3/2006 | Deppermann |
| 2007/0048872 | A1 | 3/2007 | Deppermann et al. |
| 2007/0207485 | A1 | 9/2007 | Deppermann et al. |
| 2008/0113367 | A1 | 5/2008 | Becker et al. |
| 2008/0131254 | A1 | 6/2008 | Cope et al. |
| 2008/0131924 | A1 | 6/2008 | Cope et al. |
| 2008/0317279 | A1 | 12/2008 | Deppermann et al. |
| 2009/0025288 | A1 | 1/2009 | Deppermann et al. |
| 2009/0061449 | A1 | 3/2009 | Osborn et al. |
| 2009/0215060 | A1 | 8/2009 | Deppermann et al. |
| 2009/0320955 | A1 | 12/2009 | Becker et al. |
| 2010/0044356 | A1 | 2/2010 | Cope |
| 2010/0086963 | A1 | 4/2010 | Deppermann et al. |
| 2010/0196950 | A1 | 8/2010 | Deppermann et al. |
| 2010/0263087 | A1 | 10/2010 | Deppermann et al. |
| 2010/0299790 | A1 | 11/2010 | Deppermann et al. |
| 2011/0081716 | A1 | 4/2011 | Deppermann |
| 2011/0129836 | A1 | 6/2011 | Deppermann et al. |
| 2011/0217700 | A1 | 9/2011 | Deppermann et al. |
| 2011/0296930 | A1 | 12/2011 | Deppermann et al. |
| 2012/0021411 | A1 | 1/2012 | Deppermann |
| 2012/0079629 | A1 | 3/2012 | Deppermann |
| 2012/0117865 | A1 | 5/2012 | Deppermann |
| 2012/0180386 | A1 | 7/2012 | Deppermann et al. |
| 2012/0288854 | A1 | 11/2012 | Deppermann et al. |
| 2013/0167257 | A1 | 6/2013 | Deppermann et al. |
| 2013/0260366 | A1 | 10/2013 | Deppermann et al. |
| 2014/0020287 | A1 | 1/2014 | Deppermann et al. |
| 2015/0164011 | A1 | 6/2015 | Deppermann |
| 2015/0241322 | A1 | 8/2015 | Deppermann et al. |
| 2016/0313220 | A1 | 10/2016 | Deppermann et al. |
| 2017/0196161 | A1 | 7/2017 | Deppermann et al. |
| 2018/0271042 | A1 | 9/2018 | Butruille et al. |

FOREIGN PATENT DOCUMENTS

| CL | 2190-05 | 5/2007 |
|---|---|---|
| CN | 1118235 A | 3/1996 |
| CN | 2510248 | 9/2002 |
| CN | 101052295 | 10/2007 |
| CN | 101080165 | 11/2007 |
| CN | 101437391 | 5/2009 |
| CN | 101573602 A | 11/2009 |
| CN | 101772300 A | 7/2010 |
| DE | 100 48 643 A1 | 5/2001 |
| DE | 200 22 666 | 1/2002 |
| EP | 0127313 | 7/1989 |
| EP | 1126268 A1 | 8/2001 |
| EP | 1401589 | 1/2003 |
| EP | 1862051 A2 | 12/2007 |
| EP | 2279658 | 2/2011 |

(56) References Cited

FOREIGN PATENT DOCUMENTS

| | | |
|---|---|---|
| GB | 1151988 | 5/1969 |
| GB | 1471076 | 4/1977 |
| JP | 2002 346483 | 12/2002 |
| RU | 2229210 | 5/2004 |
| SU | 536785 | 11/1976 |
| SU | 1658858 | 6/1991 |
| SU | 1805835 A3 | 3/1993 |
| WO | WO 98/14046 | 4/1998 |
| WO | WO 01/89288 | 11/2001 |
| WO | WO 02/059586 | 8/2002 |
| WO | WO 03/084847 | 10/2003 |
| WO | WO 03/100381 | 12/2003 |
| WO | WO 2004/063333 | 7/2004 |
| WO | WO 2005/031367 | 5/2005 |
| WO | WO 2006/026466 | 3/2006 |
| WO | WO 2006/026467 | 3/2006 |
| WO | WO 2007/025250 | 3/2007 |
| WO | WO 2007/103769 | 9/2007 |
| WO | WO 2008/150798 | 12/2008 |
| WO | WO 2012/012411 | 1/2012 |

OTHER PUBLICATIONS

Arumuganathan, K. & Earle, E.D., *Estimation of Nuclear DNA Content of Plants by Flow Cytometry*, Plant Molecular Biology Reporter 9(3):229-241 (1991).

Benito et al., Rapid identification of Triticeae genotypes from single seeds using the polymerase chain reaction, Plant Molecular Biology 21:181-183, 1993, 3 pages.

Bor-Yaw Lin, Ploidy Barrier to Endosperm Development in Maize (Genetics 107:103-115), May 1984, 13 pages.

Brumback, Jr., et al., "Automating fatty acid analyses from seeds: from field samples to data bases," Lab. Inf. Manage., 21 (1993) pp. 215-222.

Cabrera et al., Open Storage of Soybean Seed in Mississippi, Mississippi Agricultural and Forestry Experiment Station, Sep. 2002. <http://msucares.com/pubs/techbulletins/tb204.htm>.

Callaway A. S. et al., "High-Throughput Transgene Copy Number Estimation by Competitive PCR", Plant Molecular Biology Reporter, vol. 20, Sep. 2002, pp. 265-277.

Chenault et al., A Non-destructive Seed Sampling Method for PCR-based Analyses in Marker Assisted Selection and Transgene Screening, Peanut Science, 34:38-43 (2007).

Chunwongse J., et al., "Pre-germination genotyping screening using PCR amplification of half-seeds", Theoretical and Applied Genetics, Springer, Berlin, DE, vol. 86, No. 6, Jan. 1993, pp. 694-698.

Churchill, F., *William Johannsen and the Genotype Concept*, Journal of the History of Biology, 7(1):5-30 (1974).

Concibido, V.C. et al., *Introgression of a quantitative trait locus for yield from Glycine soja into commercial soybean cultivars*, Theor. Appl. Genet. 106:575-582 (2003).

Dahmer et al., "A Rapid Screening Technique for Determining the Lipid Composition of Soybean Seeds", Journal of the American Oil Chemists' Society, Springer, Berlin, DE, vol. 66, Jan. 1989, pp. 543-549.

Demidov Dimitri et al., "Additive effects of the feed-back insensitive bacterial aspartate kinase and the Brazil nut 2S albumin on the methionine content of transgenic narbon bean (*Vicia narbonensis* L.).", Molecular Breeding, vol. 11, No. 3, Apr. 2003, pp. 187-201.

Eder, J. & Chalyk, S., In vivo *haploid induction in maize*, Theor. Appl. Genet., 104:703-708 (2002).

Frisch, M. et al., *Comparison of Selection Strategies for Marker-Assisted Backcrossing of a Gene*, Crop Science 39:1295-1301 (1999).

Gao et al., Development of a seed DNA-based genotyping system for marker-assisted selection in maize, Moi Breeding, 22:477-494 (2008).

Gao et al., Revisiting the Hetero-Fertilization Phenomenon in Maize, PLoS ONE, vol. 6, Issue 1, Jan. 2011, 7 pages.

Gardisser D., On-Farm Drying and Storing, Chapter 15, Dec. 2004, 5 pages http://www.uaex.edu/other_areas/publications/PDF/MP197/chapter15.pdf.

Gillaspie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.

Groos, C. et al., *Study of the relationship between pre-harvest sprouting and grain color by quantitative trait loci analysis in a whitexred grain bread-wheat cross*, Theor. Appl. Genet. 104:39-47 (2002).

Guidetti Geri, (1998) Viability Myths, <http://waltonfeed.com/self/upack/ag506a1.html>, 4 pages, printed Jun. 21, 2007.

He, L. & Wang, K., *A 384-Well Microtiter-Plate-Based Template Preparation and Sequencing Method*, PCR Cloning Protocols 411-416 (2nd. ed., Humana Press 2002).

Higley P M et al., "Evaluation of Seed Biopsy Methods for Nondestructive Seed Health Testing", Phytopathology, St. Paul, MN, US, vol. 79, No. 10, Jan. 1989, p. 1140.

Horigane et al., *Two-dimensional analysis of kernels using a new sample preparation method*, Chemistry and Biology, 41(6):398-402, Jun. 25, 2003 (Published in Japanese—an English language translation is included).

Horigane, A. et al., *Evaluation of Color Characteristics of Cross-Sectioned Wheat Kernels*, Food Science & Technology Research 9(4):327-331 (2003).

J.P. Hazebroek, "Analysis of genetically modified oils" Progress in Lipid Research 39 (2000) pp. 477-506.

Jones D A L M Barber et al., "An analysis of seed development in *Pisum sativum* L. XVI. Assessing variation for fatty acid content by use of a non-destructive technique for single-seed analysis", Plant Breeding, vol. 114, No. 1, 1995, pp. 81-83.

Jousse et al., Rapid, cost-effective screening of flax genotypes to identify desirable fatty acid compositions, Electronic Journal of Plant Breeding, 1(6):1396-1404 (2010).

Kamiya et al., Rapid DNA Extraction Method from Soybean Seeds, Breeding Science 53:277-279 (2003).

Kang et al., A Rapid DNA Extraction Method for RFLP and PCR Analysis from a Single Dry Seed, Plant Molecular Biology Reporter, 16:1-9 (1998).

Karcz Jagna et al., "Structural and embryological studies of diploid and tetraploid *Arabidopsis thaliana* (L.) Heynah", Acta Biologica Cracoviensia Series Botanica, vol. 42, No. 2, 2000, pp. 113-124.

Kato, A., *Chromosome doubling of haploid maize seedlings using nitrous oxide gas at the flower primordial stage*, Plant Breeding 121:370-377 (2002).

Kisha, T.J. et al., *Genetic Diversity among Soybean Plant Introductions and North American Germplasm*, Crop Science 38:1669-1680 (1998).

Kotyk et al., High-Throughput Determination of Oil Content in Corn Kernels Using Nuclear Magnetic Resonance Imaging, JAOCS, vol. 82, No. 12, 2005, pp. 855-862.

Kramer et al., *Transgenic Avidin Maize is Resistant to Storage Insect Pests*, Nature Biotechnology, vol. 18, Jun. 2000, pp. 670-674.

Krisnangkura K. et al., "Continuous transmethylation of palm oil in an organic solvent", Jaoch, vol. 69, 1992.

Kristensen et al., A Non-Destructive Screening Method for Proanthocyanidin-Free Barley Mutants, Carlsberg Res. Commun., vol. 51, p. 509-513 (1986).

Krysan, Breakthrough Technologies, Ice-Cap. A High-Throughput Method for Capturing Plant Tissue Samples for Genotype Analysis, Plant Physiology, Jul. 2004 vol. 135, pp. 1162-1169.

Li et al., Molecular Mapping Genes Conditioning Reduced Palmitic Acid Content in N87-2122-4 Soybean (Crop Science 42:373-378), 2002, 6 pages.

Lipman et al., *Tolerance of Liquid-Air Temperature by Seeds of Higher Plants for Sixty Days*, Plant Physiology 392-394 (1934).

Manabe et al., Segregation distortion through female gametophates in interspecific hybrids of tetraploid wheat as revealed by RAPD analysis (Hereditas 131: 47-53), Oct. 1999, 7 pages.

McCarthy, Paul L., et al., "Rapid identification of transformed wheat using a half-seed PCR assay", Biotechniques, vol. 31, No. 3, Mar. 2002, pp. 560-564.

(56) References Cited

OTHER PUBLICATIONS

Meru et al., A non-destructive genotyping system from a single seed for marker-assisted selection in watermelon, GMR Genetics and Molecular Research 12(1):702-709 (2013).

Morrison, *Sampling in Seed Health Testing*, The American Phytopathology, 1999, 89: 1084-1087.

Notice of Opposition to European Patent EP 1869961 (Application No. EP07016960.2), as filed by Syngenta Crop Protection AG, and related filings including decision to maintain the European Patent, Oct. 25, 2012, 117 pages.

Notice of Opposition to European Patent EP 1991043 (Application No. 07757774.0), as filed by Syngenta Crop Protection AG, and related filings including decision to maintain the European Patent, Feb. 18, 2011, 173 pages.

Notice of Opposition to European Patent EP 2279657 (Application No. EP10184375.3), as filed by Syngenta Crop Protection AG, and related filings, Dec. 11, 2013, 39 pages.

Petition for Inter Partes Review of U.S. Pat. No. 7,832,143 as filed by E.I. du Pont de Nemours and Company on Jan. 8, 2014, 70 pages, (and 24 Exhibits); Patent Owner's Preliminary Response, dated Apr. 22, 2014, to the Petition for Inter Partes Review; and Patent Trial and Appeal Board's Decision, dated Jul. 11, 2014, Denying Institution of Inter Partes Review.

Petition for Inter Partes Review of U.S. Pat. No. 8,028,469 as filed by E.I. du Pont de Nemours and Company on Jan. 8, 2014, 51 pages, (and 25 Exhibits); Patent Owner's Preliminary Response, dated Apr. 22, 2014, to the Petition for Inter Partes Review; and Patent Trial and Appeal Board's Decision, dated Jul. 21, 2014, Denying Institution of Inter Partes Review.

Petition for Inter Partes Review of U.S. Pat. No. 8,071,845 as filed by E.I. du Pont de Nemours and Company on Jan. 8, 2014, 60 pages, (and 25 Exhibits); Patent Owner's Preliminary Response, dated Apr. 22, 2014, to the Petition for Inter Partes Review; and Patent Trial and Appeal Board's Decision, dated Jul. 11, 2014, Denying Institution of Inter Partes Review.

Petition for Inter Partes Review of U.S. Pat. No. 8,245,439 as filed by E.I. du Pont de Nemours and Company on Jan. 8, 2014, 69 pages, (and 27 Exhibits); Patent Owner's Preliminary Response, dated Apr. 22, 2014, to the Petition for Inter Partes Review; and Patent Trial and Appeal Board's Decision, dated Jul. 11, 2014, Denying Institution of Inter Partes Review.

Petition for Inter Partes Review of U.S. Pat. No. 8,312,672 as filed by E.I. du Pont de Nemours and Company on Jan. 8, 2014, 71 pages, (and 34 Exhibits); Patent Owner's Preliminary Response, dated Apr. 14, 2014, to the Petition for Inter Partes Review; and Patent Trial and Appeal Board's Decision, dated Jul. 11, 2014, Denying Institution of Inter Partes Review.

Pioneer Hi-Bred International, Inc., Downloadable Photos—Laser-Assisted Seed Selection, http://www.pioneer.com/web/site/portal/menuiteam.b9e99dcb8e2cfd8ecfe6d10093a0/, printed as of Nov. 25, 2008, 4 pages.

R.K. Downey, Genetic Control of Fatty Acid Biosynthesis in Rapeseed (*Brassica napus* L.) (AOCS 41:475-478), 1964, 4 pages.

R.K.Downey, Methods of Breeding for Oil Quality in Rape (Canadian Journal of Plant Science 43:271-275), Jul. 1963, 7 pages.

Schuster Ivan et al., "Correlation between high molecular weight gluten subunits composition and bread-making quality in Brazilian wheat", Brazilian Journal of Genetics, vol. 20, No. 4, Dec. 1997, pp. 667-671.

Sedcole, J.R. "Number of plants necessary to recover a trait," Crop Sci. 17:667 (1977).

Serial Extraction of Endosperm Drillings (SEED)—A Method for Detecting Transgenes and Proteins in Single Viable Maize Kernels, Varapom Sangton, et al., Plant Molecular Biology Reporter 19: 151-158, Jun. 2001, International Society for Plant Molecular Biology.

Smith et al., *Genetic Purity and Testing Technologies for Seed Quality: A Company Perspective*, Seed Science Research, 1998, vol. 8, pp. 285-293.

Tanksley et al., Seed Banks and Molecular Maps: Unlocking Genetic Potential from the Wild (Science 277:1063-1066) Aug. 1997, 5 pages.

Van Der Mey J A M et al., "Mass Screening for Alkaloid Content in Lupinus-Albus", Applied Plant Science, vol. 1, No. 2, 1987, pp. 80-82.

Varshney et al., Plant Biotechnology and Molecular Markers (Kluwer Academic Publishers; Print ISBN: 1-4020-1911-4; Edited by P.S. Srivastava, Alka Narula, Sheela Srivastava) (Chapter 20), Apr. 2004, 42 pages.

Von Post et al., A High-Throughput DNA Extraction Method for Barley Seed, Euphytica 130: 255-260, 2003.

Wright, H., *Commercial Hybrid Seed Production*, Hybridization of Crop Plants 161-176 (1980).

Zeile, W.L. et al., "A Rapid Non-Destructive Technique for Fatty Acid Determination in Individual Peanut Seed" Peanut Science (1993) 20:9-11 (3 pages).

SU 1805835 A3 is not in the English language; an English language translation is provided thereto for convenience to the Examiner.

DE 200 22 666 U1 is not in the English language. An English language abstract is not available. Please refer to the drawings for relevance.

JP 2002346483A is not in the English language, but an English language abstract is included.

CN 2510248 is not in the English language. However, an English language translation of this reference has been provided.

Horigane et al., *Two-dimensional analysis of kernels using a new sample preparation method*, Chemistry and Biology, 41(6):398-402, Jun. 25, 2003, is not in the English language. However, an English language translation of this reference has been provided.

CN 1118235 is not in the English language, but an English language abstract is included.

CN 101573602 is not in the English language, but an English language abstract is included. Also CN 101573602 generally corresponds to U.S. Pat. No. 7,915,006 listed in the attached Form 1449.

CN 101772300 is not in the English language but an English language abstract is included. Also CN 101772300 generally corresponds to U.S. Pat. No. 8,189,901 listed in the attached Form 1449.

SU 536785 is not in the English language. An English language abstract is not available. Please refer to the drawings for relevance.

SU 1658858 is not in the English language. An English language abstract is not available. Please refer to the drawings for relevance.

DE 100 48 643 is not in the English language, but an English language abstract is included.

CL 1035-03 is not in the English language and generally corresponds to WO 03/100381 listed in the attached Form 1449.

CL 673-03 is not in the English language and generally corresponds to U.S. Pat. No. 7,044,306 listed in the attached Form 1449.

CL 2190-05 is not in the English language and generally corresponds to US 2006/0042528 listed in the attached Form 1449.

RU 2229210 is not in the English language, but an English language abstract is included.

CN 101052295 is not in the English language and generally corresponds to US 2006/0042528 listed in the attached Form 1449.

CN 101080165 is not in the English language and generally corresponds to U.S. Pat. No. 7,502,113 listed in the attached Form 1449.

CN 101437391 is not in the English language and generally corresponds to U.S. Pat. No. 7,998,669 listed in the attached Form 1449.

U.S. Appl. No. 11/213,430: (a) Restriction Requirement dated Jul. 5, 2007; (b) Office Action dated Nov. 15, 2007; (c) Notice of Allowance and Fee(s) Due dated Jun. 13, 2008; and (d) Supplemental Notice of Allowability, dated Dec. 26, 2008 all issued in U.S. Appl. No. 11/213,430 (which has at least one inventor in common with the current application).

U.S. Appl. No. 11/213,431: (a) Restriction Requirement dated Apr. 2, 2009; (b) Office Action dated Sep. 3, 2009; and (c) Notice of Allowance and Fee(s) Due, dated May 19, 2010 all issued in U.S. Appl. No. 11/213,431 (which has at least one inventor in common with the current application).

(56) References Cited

OTHER PUBLICATIONS

U.S. Appl. No. 11/213,432: (a) Restriction Requirement dated Oct. 31, 2008; (b) Office Action dated Feb. 3, 2009; and (c) Notice of Allowance and Fee(s) Due dated Aug. 10, 2009, all issued in U.S. Appl. No. 11/213,432 (which has inventors in common with the current application).
U.S. Appl. No. 11/213,434: (a) Restriction Requirement dated Apr. 5, 2007; (b) Office Action dated Jul. 2, 2007; (c) Office Action dated Nov. 13, 2007; (d) Office Action dated May 7, 2008; (e) Office Action dated Oct. 31, 2008; (f) Office Action dated Jun. 4, 2009; (g) Office Action, dated Jan. 14, 2010; and (h) Notice of Abandonment dated Aug. 20, 2010 all issued in U.S. Appl. No. 11/213,434 (which has at least one inventor in common with the current application).
U.S. Appl. No. 11/213,435: (a) Restriction Requirement dated Jul. 5, 2007; (b) Office Action dated Nov. 15, 2007; (c) Final Office Action dated Apr. 10, 2009; and (d) Notice of Allowance and Fee(s) Due dated Aug. 26, 2009 all issued in U.S. Appl. No. 11/213,435 (which has at least one inventor in common with the current application).
U.S. Appl. No. 11/680,611: (a) Restriction Requirement dated Oct. 6, 2008; (b) Office Action dated Apr. 7, 2009; and (c) Notice of Allowance dated Dec. 7, 2009 all issued in U.S. Appl. No. 11/680,611 (which has at least one inventor in common with the current application).
U.S. Appl. No. 12/243,739: (a) Restriction Requirement dated May 28, 2009; (b) Office Action dated Nov. 16, 2009; (c) Notice of Allowance dated Jul. 6, 2010; and (d) Notice of Allowance dated Oct. 8, 2010 all issued in U.S. Appl. No. 12/243,739 (which has at least one inventor in common with the current application).
U.S. Appl. No. 12/358,985: (a) Notice of Allowance dated Aug. 19, 2010; (b) Patent Owner's Preliminary Response, dated Aug. 26, 2014, to the Petition for Inter Partes Review; and (c) Patent Trial and Appeal Board's Decision, dated Jul. 11, 2014, Denying Institution of Inter Partes Review issued in U.S. Appl. No. 12/358,985 (see item in the Form 1449 filed herewith) (which has at least one inventor in common with the current application).
U.S. Appl. No. 12/563,895: (a) Office Action dated Aug. 4, 2010 and (b) Notice of Allowance dated Sep. 21, 2010 both issued in U.S. Appl. No. 12/563,895 (which has at least one inventor in common with the current application).
U.S. Appl. No. 12/759,423:(a) Restriction Requirement dated Jun. 15, 2010; (b) Notice of Allowance dated Sep. 23, 2010; and (c) Supplemental Notice of Allowance dated Nov. 5, 2010, all issued in U.S. Appl. No. 12/759,423 (which has at least one inventor in common with the current application).
U.S. Appl. No. 11/510,771: (a) Office Action dated Jan. 6, 2009; (b) Final Office Action dated May 8, 2009; (c) Office Action dated Aug. 6, 2009; (d) Final Office Action dated Apr. 6, 2010; (e) Office Action dated Mar. 14, 2011; (f) Final Office Action dated Sep. 29, 2011; and (g) Notice of Abandonment dated Apr. 18, 2012 all issued in U.S. Appl. No. 11/510,771 (which has at least one inventor in common with the current application).
U.S. Appl. No. 12/767,640: (a) Restriction Requirement dated Sep. 1, 2010 and (b) Notice of Allowance dated Jan. 10, 2011 both issued in U.S. Appl. No. 12/767,640 (which has at least one inventor in common with the current application).
U.S. Appl. No. 12/848,751: (a) Restriction Requirement dated Oct. 13, 2010; (b) Office Action dated Feb. 11, 2011; (c) Notice of Allowance dated Aug. 30, 2011; (d) Patent Owner's Preliminary Response, dated Apr. 22, 2014, to the Petition for Inter Partes Review; and (e) Patent Trial and Appeal Board's Decision, dated Jul. 11, 2014, Denying Institution of Inter Partes Review all issued in U.S. Appl. No. 12/848,751 (see item in the Form 1449 filed herewith) (which has at least one inventor in common with the current application).
U.S. Appl. No. 11/680,180: (a) Restriction Requirement dated Jan. 6, 2010; (b) Office Action dated Jun. 8, 2010; (c) Final Office Action dated Dec. 8, 2010; and (d) Notice of Allowance dated Jun. 24, 2011, all issued in U.S. Appl. No. 11/680,180 (which has at least one inventor in common with the current application).

U.S. Appl. No. 12/128,279: (a) Office Action dated Aug. 9, 2010; (b) Notice of Allowance dated Jan. 6, 2011; (c) Notice of Allowance dated May 26, 2011; (d) Patent Owner's Preliminary Response, dated Aug. 26, 2014, to the Petition for Inter Partes Review; and (d) Patent Trial and Appeal Board's Decision, dated Jul. 21, 2014, Denying Institution of Inter Partes Review all issued in U.S. Appl. No. 12/128,279 (see item #177 in the Form 1449 filed herewith) (which has at least one inventor in common with the current application).
U.S. Appl. No. 13/016,242: (a) Office Action dated May 4, 2011; (b) Office Action dated Oct. 27, 2011; (c) Office Action dated Feb. 24, 2012; (d) Final Office Action dated Jul. 3, 2012; (e) Notice of Allowance dated Oct. 29, 2012; and (f) Notice of Allowance dated Jul. 1, 2013 all issued in U.S. Appl. No. 13/016,242 (which has at least one inventor in common with the current application).
U.S. Appl. No. 12/966,715: (a) Office Action dated Feb. 17, 2012; (b) Notice of Allowance dated Aug. 21, 2012; (c) Notice of Allowance dated Jan. 9, 2013; and (d) Supplemental Notice of Allowance dated Jan. 24, 2013 all issued in U.S. Appl. No. 12/966,715 (which has at least one inventor in common with the current application).
U.S. Appl. No. 13/302,657: (a) Office Action dated Feb. 10, 2012; (b) Notice of Allowance dated Jul. 24, 2012; and (c) Notice of Allowance dated Jan. 17, 2013 all issued in U.S. Appl. No. 13/302,657 (which has at least one inventor in common with the current application).
U.S. Appl. No. 13/251,993: (a) Office Action dated Dec. 22, 2011; (b) Notice of Allowance dated Apr. 13, 2012; (c) Patent Owner's Preliminary Response, dated Aug. 26, 2014, to the Petition for Inter Partes Review; and (d) Patent Trial and Appeal Board's Decision, dated Jul. 11, 2014, Denying Institution of Inter Partes Review issued in U.S. Appl. No. 13/251,993 (see item in the Form 1449 filed herewith) (which has at least one inventor in common with the current application).
U.S. Appl. No. 13/210,212: (a) Office Action dated Dec. 23, 2011 and (b) Notice of Allowance dated May 24, 2013 issued in U.S. Appl. No. 13/210,212 (which has at least one inventor in common with the current application).
U.S. Appl. No. 13/108,762: (a) Office Action dated Aug. 4, 2011; (b) Notice of Allowance dated Jul. 20, 2012; (c) Patent Owner's Preliminary Response, dated Apr. 14, 2014, to the Petition for Inter Partes Review; and (d) Patent Trial and Appeal Board's Decision, dated Jul. 11, 2014, Denying Institution of Inter Partes Review issued in U.S. Appl. No. 13/108,762 (see item in the Form 1449 filed herewith) (which has at least one inventor in common with the current application).
U.S. Appl. No. 13/407,348: (a) Office Action dated Jul. 16, 2012 and (b) Notice of Allowance dated Apr. 1, 2013 issued in U.S. Appl. No. 13/407,348 (which has at least one inventor in common with the current application).
U.S. Appl. No. 13/556,742: (a) Office Action dated Oct. 11, 2012 and (b) Notice of Allowance dated Feb. 1, 2013 issued in U.S. Appl. No. 13/556,742 (which has at least one inventor in common with the current application).
U.S. Appl. No. 13/680,603: (a) Office Action dated Sep. 10, 2013 and (b) Notice of Allowance dated Jul. 1, 2014 issued in U.S. Appl. No. 13/680,603 (which has at least one inventor in common with the current application).
U.S. Appl. No. 14/032,850: (a) Office Action dated Dec. 10, 2013 and (b) Notice of Allowance dated Jan. 14, 2015 issued in U.S. Appl. No. 14/032,850 (which has at least one inventor in common with the current application).
U.S. Appl. No. 13/897,024: (a) Office Action dated Dec. 13, 2013 and (b) Notice of Allowance dated Dec. 3, 2014 issued in U.S. Appl. No. 13/897,024 (which has at least one inventor in common with the current application).
U.S. Appl. No. 13/186,126: (a) Office Action dated May 23, 2014 and (b) Notice of Allowance dated Dec. 5, 2014 issued in U.S. Appl. No. 13/186,126. The current application is a continuation of U.S. Appl. No. 13/186,126 and have priority claims related to U.S. Appl. No. 61/365,826.
U.S. Appl. No. 13/887,738: (a) Restriction Requirement dated Mar. 11, 2015; (b) Office Action dated Sep. 4, 2015; and (c) Notice of

(56) References Cited

OTHER PUBLICATIONS

Allowance dated May 18, 2016 issued in U.S. Appl. No. 13/887,738 (which has at least one inventor in common with the current application).
U.S. Appl. No. 14/635,738: (a) Office Action dated Feb. 26, 2016 and (b) Notice of Allowance dated Sep. 15, 2016 issued in U.S. Appl. No. 14/635,738 (which has at least one inventor in common with the current application).
U.S. Appl. No. 14/685,033: (a) Notice of Allowance dated Mar. 3, 2016 issued in U.S. Appl. No. 14/685,033 (which has at least one inventor in common with the current application).
U.S. Appl. No. 14/629,235: (a) Restriction Requirement dated Jul. 11, 2017 issued in U.S. Appl. No. 14/629,235 (which has at least one inventor in common with the current application).
PCT/US2011/044514: (a) International Search Report and Written Opinion dated Apr. 6, 2012 and (b) International Preliminary Report on Patentability (IPRP) dated Jan. 31, 2013 issued in PCT/US2011/044514. Both the instant application and PCT/US2011/044514 have priority claims related to U.S. Appl. No. 61/365,826.
AU 2011282283: (a) Office Action dated Nov. 14, 2014 and (b) Notice of Acceptance dated Dec. 14, 2015 issued in AU 2011282273. AU 2011282273 is a national phase of PCT/US2011/044514. Both the instant application and PCT/US2011/044514 have priority claims related to U.S. Appl. No. 61/365,826.
CA 2,805,434: (a) Office Action dated Apr. 20, 2017 issued in CA 2,805,434. CA 2,805,434 is a national phase of PCT/US2011/044514. Both the instant application and PCT/US2011/044514 have priority claims related to U.S. Appl. No. 61/365,826.
CN 201180045241.2: (a) Office Action dated Feb. 21, 2014; (b) Chinese Search Report dated Feb. 21, 2014; (c) Office Action dated Jan. 12, 2015; and (d) Notification of Grant dated Mar. 2, 2016 issued in CN 201180045241.2. CN 201180045241.2 is a national phase of PCT/US2011/04454. Both the instant application and PCT/US2011/044514 have priority claims related to U.S. Appl. No. 61/365,826. The Search Report was included with an Office Action issued in this Chinese Application on Feb. 21, 2014.
MX/a/2013/000790: (a) Office Action dated Jan. 23, 2015 and (b) Notice of Allowance dated Sep. 4, 2015 issued in MX/a/2013/000790. MX/a/2013/000790 is a national phase of PCT/US2011/044514. The Office Action is not in the English language. English language comments pertaining thereto are provided for convenience to the Examiner. Both the instant application and PCT/US2011/044514 have priority claims related to U.S. Appl. No. 61/365,826.
ZA 2013/00457: (a) Notice of Acceptance dated Dec. 2, 2015 issued in ZA 2013/00457. ZA 2013/00457 is a national phase of PCT/US2011/04451. Both the instant application and PCT/US2011/044514 have priority claims related to U.S. Appl. No. 61/365,826.
EP 10184375.3: (a) One additional filing relating to the Notice of Opposition to European Patent EP 2279657 (Application No. EP10184375.3) (see item in the Form 1449 filed herewith), including (b) Summons to Attend Oral Proceedings and Preliminary Decision of Opposition Division dated Jan. 26, 2015.
EP 07016960.2: (a) Three additional filings relating to the Notice of Opposition to European Patent EP 1869961 (Application No. EP07016960.2) (see item in the Form 1449 filed herewith), including (b) Notice of Appeal dated Oct. 7, 2014; (c) Grounds of Appeal dated Dec. 5, 2014; and (d) Opponent's Grounds of Appeal dated Dec. 8, 2014.
U.S. Appl. No. 11/213,432 (now U.S. Pat. No. 7,591,101 issued Sep. 22, 2009), filed Aug. 26, 2005, Deppermann.
U.S. Appl. No. 11/213,430 (now U.S. Pat. No. 7,502,113 issued Mar. 10, 2009), filed Aug. 26, 2005, Deppermann et al.
U.S. Appl. No. 11/213,434 (abandoned), filed Aug. 26, 2005, Deppermann et al.
U.S. Appl. No. 11/213,431 (now U.S. Pat. No. 7,767,883 issued Aug. 3, 2010), filed Aug. 26, 2005, Deppermann et al.
U.S. Appl. No. 11/213,435 (now U.S. Pat. No. 7,611,842 issued Nov. 3, 2009), filed Aug. 26, 2005, Deppermann et al.
U.S. Appl. No. 12/243,739 (now U.S. Pat. No. 7,830,516 issued Nov. 9, 2010), filed Oct. 1, 2008, Deppermann et al.
U.S. Appl. No. 11/680,611 (now U.S. Pat. No. 7,703,238 issued Apr. 27, 2010), filed Feb. 28, 2007, Deppermann et al.
U.S. Appl. No. 12/358,985 (now U.S. Pat. No. 7,832,143 issued Nov. 16, 2010), filed Jan. 23, 2009, Deppermann et al.
U.S. Appl. No. 11/680,180 (now U.S. Pat. No. 7,998,669 issued Aug. 16, 2011), filed Feb. 28, 2007, Deppermann et al.
U.S. Appl. No. 11/510,771 (abandoned), filed Aug. 25, 2006, Deppermann et al.
U.S. Appl. No. 12/128,279 (now U.S. Pat. No. 8,028,469 issued Oct. 4, 2011), filed May 28, 2008, Deppermann et al.
U.S. Appl. No. 12/563,895 (now U.S. Pat. No. 7,849,632 issued Dec. 14, 2010), filed Sep. 21, 2009, Deppermann et al.
U.S. Appl. No. 12/579,423 (now U.S. Pat. No. 7,877,926 issued Feb. 1, 2011), filed Apr. 13, 2010, Deppermann et al.
U.S. Appl. No. 12/848,751 (now U.S. Pat. No. 8,071,845 issued Dec. 6, 2011), filed Aug. 2, 2010, Deppermann et al.
U.S. Appl. No. 12/767,640 (now U.S. Pat. No. 7,941,969 issued May 17, 2011), filed Apr. 26, 2010, Deppermann et al.
U.S. Appl. No. 13/108,762 (now U.S. Pat. No. 8,312,672 issued Nov. 30, 2012), filed May 16, 2011, Deppermann et al.
U.S. Appl. No. 13/016,242 (now U.S. Pat. No. 8,561,346 issued Oct. 22, 2013), filed Jan. 28, 2011, Deppermann et al.
U.S. Appl. No. 12/966,715 (now U.S. Pat. No. 8,434,259 issued May 7, 2013), filed Dec. 13, 2010, Deppermann et al.
U.S. Appl. No. 13/302,657 (now U.S. Pat. No. 8,436,225 issued May 7, 2013), filed Nov. 22, 2011, Deppermann et al.
U.S. Appl. No. 13/186,126 (now U.S. Pat. No. 9,003,696 issued Apr. 14, 2015), filed Jul. 19, 2011, Deppermann et al.
U.S. Appl. No. 13/251,993 (now U.S. Pat. No. 8,245,439 issued Aug. 21, 2012), filed Oct. 3, 2011, Deppermann et al.
U.S. Appl. No. 13/210,212 (now U.S. Pat. No. 8,539,713 issued Sep. 24, 2013), filed Aug. 15, 2011, Deppermann et al.
U.S. Appl. No. 13/407,348 (now U.S. Pat. No. 8,501,480 issued Aug. 6, 2013), filed Feb. 28, 2012, Deppermann et al.
U.S. Appl. No. 13/556,742 (now U.S. Pat. No. 8,443,545 issued May 21, 2013), filed Jul. 24, 2012, Deppermann et al.
U.S. Appl. No. 13/680,603 (now U.S. Pat. No. 8,959,833 issued Feb. 24, 2015), filed Nov. 19, 2012, Deppermann et al.
U.S. Appl. No. 13/887,738 (now U.S. Pat. No. 9,448,141 issued Sep. 20, 2016), filed May 6, 2013, Deppermann.
U.S. Appl. No. 13/897,024 (now U.S. Pat. No. 8,997,398 issued Apr. 7, 2015), filed May 17, 2013, Deppermann et al.
U.S. Appl. No. 14/032,850 (now U.S. Pat. No. 9,027,278 issued May 12, 2015), filed Sep. 20, 2013, Deppermann et al.
U.S. Appl. No. 14/629,235, filed Feb. 23, 2015, Deppermann et al.
U.S. Appl. No. 14/635,738 (now U.S. Pat. No. 9,551,636 issued Jan. 24, 2017), filed Mar. 2, 2015, Deppermann et al.
U.S. Appl. No. 14/685,033 (now U.S. Pat. No. 9,383,291 issued Jul. 5, 2016), filed Apr. 13, 2015, Deppermann et al.
U.S. Appl. No. 15/200,411, filed Jul. 1, 2016, Deppermann et al.
U.S. Appl. No. 15/268,235, filed Sep. 16, 2016, Deppermann.
U.S. Appl. No. 15/411,531, filed Jan. 20, 2017, Deppermann et al.
U.S. Appl. No. 15/268,235: (a) Notice of Allowance dated Jul. 18, 2018 issued in U.S. Appl. No. 15/268,235 (which has at least one inventor in common with the current application).
U.S. Appl. No. 15/200,411: (a) Notice of Allowance dated Nov. 28, 2018 issued in U.S. Appl. No. 15/200,411 (which has at least one inventor in common with the current application).
U.S. Appl. No. 15/411,531: (a) Office Action dated Oct. 29, 2018 issued in U.S. Appl. No. 15/411,531 (which has at least one inventor in common with the current application).
AR P11 01 02624: (a) Office Action dated Nov. 5, 2018 issued in Argentina Application No. P11 01 02624. The Official Action is not in the English language. Applicant provides an English language translation for convenience to the Examiner. AR P11 01 02624 and the instant application have priority claims related to U.S. Appl. No. 61/365,826.
BR 112013001330-3: (a) Office Action dated Mar. 29, 2018 issued in Brazilian Application No. 112013001330-3. BR 112013001330-3 is a national phase of PCT/US2011/044514. The Official Action is not in the English language. Applicant provides an Informal English language translation for convenience to the Examiner. Both the

(56) References Cited

OTHER PUBLICATIONS instant application and PCT/US2011/044514 have priority claims related to U.S. Appl. No. 61/365,826.

EP 10184375.3: One additional filing relating to the Notice of Opposition to European Patent EP 2279657 (Application No. EP10184375.3) (see item in the Form 1449 previously filed Jul. 20, 2017) including (a) Summons to Attend Oral Proceedings dated Jun. 26, 2018 (which has at least one inventor in common with the current application).

EP 07016960.2: One additional filings relating to the Notice of Opposition to European Patent EP 1869961 (Application No. EP07016960.2) (see item in the Form 1449 previously filed Jul. 20, 2017), including (a) Decision of Technical Board of Appeal dated Apr. 5, 2018 (which has at least one inventor in common with the current application).

U.S. Appl. No. 15/996,080, filed Jun. 1, 2018, Deppermann.

U.S. Appl. No. 16/193,536, filed Nov. 16, 2018, Deppermann.

U.S. Appl. No. 16/376,415, filed Apr. 15, 2019, Deppermann et al.

U.S. Appl. No. 16/625,386, filed Dec. 20, 2019, Brown et al.

U.S. Appl. No. 16/193,536: (a) Office Action dated Mar. 7, 2019 and (b) Restriction Requirement dated Oct. 22, 2019. U.S. Appl. No. 16/193,536 has at least one inventor in common with the current application.

U.S. Appl. No. 15/411,531: (a) Final Office Action dated May 9, 2019 and (b) Notice of Allowance dated Sep. 11, 2019. U.S. Appl. No. 15/411,531 has at least one inventor in common with the current application.

U.S. Appl. No. 15/996,080: (a) Restriction Requirement dated Dec. 23, 2019. U.S. Appl. No. 15/996,080 has at least one inventor in common with the current application.

AR P11 01 02624: (a) Office Action dated May 20, 2019. The Official Action is not in the English language. Applicant provides an English language summary for convenience to the Examiner. Argentine Application P11 01 02624 and the instant application have priority claims related to U.S. Appl. No. 61/365,826.

BR 112013001330-3: (a) Notice of Allowance dated Jan. 17, 2019. Brazilian Application No. 112013001330-3 is a national phase of PCT/US2011/044514. Both the instant application and PCT/US2011/044514 have priority claims related to U.S. Appl. No. 61/365,826.

In 541/DELNP/2013: (a) First Examination Report dated Jan. 9, 2019. India Application No. 541/DELNP/2013 is a national phase of PCT/US2011/044514. Both the instant application and PCT/US2011/044514 have priority claims related to U.S. Appl. No. 61/365,826.

EP 10184375.3: Two additional filing relating to the Notice of Opposition to European Patent EP 2279657 (Application No. EP10184375.3) (see item in the Form 1449 previously filed Jul. 20, 2017) including (a) Minutes from the Oral Proceedings dated Feb. 27, 2019 and (b) Decision of Technical Board of Appeal dated Mar. 11, 2019. European Patent EP 2279657 has at least one inventor in common with the current application.

AUTOMATED SYSTEMS FOR REMOVING TISSUE SAMPLES FROM SEEDS, AND RELATED METHODS

CROSS-REFERENCE TO RELATED APPLICATION

This application is a continuation of U.S. patent application Ser. No. 13/186,126, filed Jul. 19, 2011, which claims priority to (and the benefit of) U.S. Provisional Application No. 61/365,826, filed on Jul. 20, 2010. The disclosures of each of these applications are incorporated herein by reference in their entireties.

FIELD

The present disclosure generally relates to automated systems and methods for removing tissue samples from biological materials such as, for example, seeds, etc.

BACKGROUND

This section provides background information related to the present disclosure which is not necessarily prior art.

In plant development and improvement, genetic improvements are made in the plant, either through selective breeding or genetic manipulation, and when a desirable improvement is achieved, a commercial quantity is developed, or bulked, by planting and harvesting seeds over several generations. However, not all harvested seeds express the desired traits and, thus, these seeds need to be culled from the bulked quantity. To hasten the process of bulking up the quantity of seeds, statistical samples may be taken and tested to cull seeds (or groups of seeds associated with the statistical samples) from the seeds that do not adequately express the desired trait.

SUMMARY

This section provides a general summary of the disclosure, and is not a comprehensive disclosure of its full scope or all of its features.

According to one aspect of the present disclosure, a seed sampling system includes an automated seed loading assembly operable to singulate seeds from a plurality of seeds within the seed bin, an automated seed sampling assembly operable to remove tissue samples from the singulated seeds, and an automated seed transport assembly operable to transfer the singulated seeds from the seed loading assembly to the seed sampling assembly. The seed transport assembly includes multiple retention members. Each of the retention members is movable relative to the seed loading assembly and to the seed sampling assembly. The seed transport assembly is operable to position one of the multiple retention members adjacent to the seed loading assembly for engaging one of the singulated seeds, while positioning another of the retention members adjacent to the seed sampling assembly for presenting another of the singulated seeds to the seed sampling assembly.

According to another aspect of the present disclosure, a seed sampling system includes an automated seed loading assembly including a seed bin and operable to separate individual seeds from a plurality of seeds within the seed bin, an automated seed transport assembly including a transport carousel and multiple banks of retention members mounted on the transport carousel, and an automated seed sampling assembly including multiple automated samplers linearly disposed adjacent to the transport carousel. Each of the multiple automated samplers is operable to remove a tissue sample from a seed. The transport carousel is configured to rotate about an axis to transport the multiple banks of retention members between the samplers and the seed loading assembly. The axis of rotation of the transport carousel is substantially parallel to a linear axis defined by the disposition of the samplers.

According to yet another aspect of the present disclosure, an automated method for removing tissue samples from seeds is disclosed. The method includes singulating a seed from a plurality of seeds, engaging the singulated seed with a retention member of an automated seed transport assembly, rotating the seed transport assembly about an axis to move the retention member and singulated seed to a position adjacent a sampler of an automated seed sampling assembly, and removing a tissue sample from the singulated seed at the sampler.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1. is a perspective view of a seed sampling system including one or more aspects of the present disclosure and configured to singulate seeds and remove tissue samples from the singulated seeds;

Corresponding reference numerals indicate corresponding parts throughout the several views of the drawings.

DETAILED DESCRIPTION

Example embodiments will now be described more fully with reference to the accompanying drawings. FIGS. 1-9 illustrate an example embodiment of an automated seed sampling system 10 including one or more aspects of the present disclosure. The illustrated system 10 is suitable for use in removing samples from biological materials. Samples may include, for example, tissue samples, etc. And, biological materials may include, for example, seeds (e.g., soybeans, corn, wheat, cotton, etc.), etc. The example embodiment is provided for illustrative purposes only, and may be used in connection with one or more of the methods disclosed herein.

Figure 1:
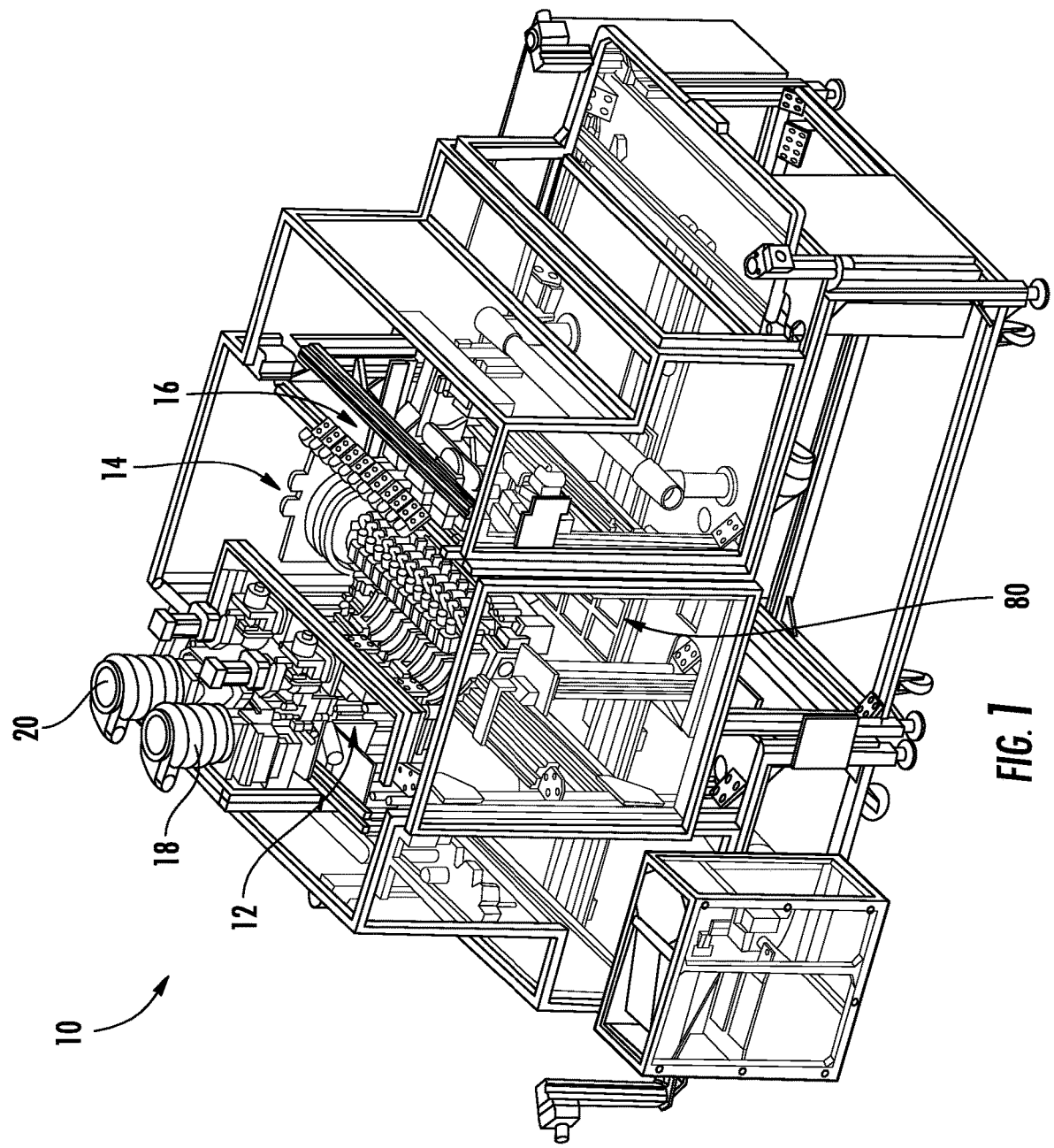

As shown in FIG. 1, the automated seed sampling system 10 generally includes an automated seed loading assembly 12, an automated seed transport assembly 14, and an automated seed sampling assembly 16. Generally, the seed loading assembly 12 operates to singulate (or isolate, etc.) individual seeds from a quantity (e.g., a plurality, etc.) of seeds. The transport assembly 14 then operates to move the singulated seeds from the seed loading assembly 12 to the seed sampling assembly 16 where tissue samples are removed from the singulated seeds. The tissue samples may be subsequently analyzed to determine if the seeds, from which the tissue samples were taken, exhibit or do not exhibit one or more desired traits.

Operation of the seed loading assembly 12, seed transport assembly 14, and seed sampling assembly 16 is automated and may be controlled (and coordinated), for example, by a central control system within the scope of the present disclosure. In addition, components of the seed loading assembly 12, seed transport assembly 14, and/or seed sampling assembly 16 may be pneumatically operated using, for example, efficient air flows of about ten cubic feet per minute or less, etc. Such pneumatic operations may apply to moving seeds through the seed sampling system 10 and between the assemblies 12, 14, 16. Such pneumatic operations may include drawing seeds through the seed sampling system 10 (e.g., via vacuum processes, etc.), forcing seeds through the system 10 (e.g., via air jets, etc.), and/or combinations thereof, for example, to help inhibit damage of seeds during transport, etc.

In the illustrated embodiment, the seed loading assembly 12, seed transport assembly 14, and seed sampling assembly 16 are supported by various structures such as stationary braces, beams, platforms, pedestals, stands, etc. Although such structures are necessary to the construction of the seed sampling system 10, description of their placement, orientation and interconnections are not necessary for one skilled in the art to easily and fully comprehend the structure, function and operation of the seed sampling system 10. Particularly, such structures are clearly illustrated throughout the figures and, as such, their placement, orientation and interconnections are easily understood by one skilled in the art.

With continued reference to FIG. 1, seed hoppers 18, 20 are provided for receiving seeds into the sampling system 10 as desired and funneling the seeds to the seed loading assembly 12. The seed hoppers 18, 20 may be configured (e.g., sized, shaped, constructed, etc.) to receive any desired type of seeds (e.g., soybean, corn, wheat, cotton, etc.) and/or any desired quantity of seeds within the scope of the present disclosure. For example, in the illustrated embodiment the seed hoppers 18, 20 may each have a capacity to receive (and funnel) about 4,500 soybeans to the seed loading assembly 12. Agitators (e.g., mechanical mixers, air jets, vibratory devices, etc.) may be provided within the seed hoppers 18, 20 to promote movement of seeds to the seed loading assembly 12 and help inhibit seeds from bridging (or forming voids), sticking, bunching, etc. at locations in the seed hoppers 18, 20.

Figure 2:
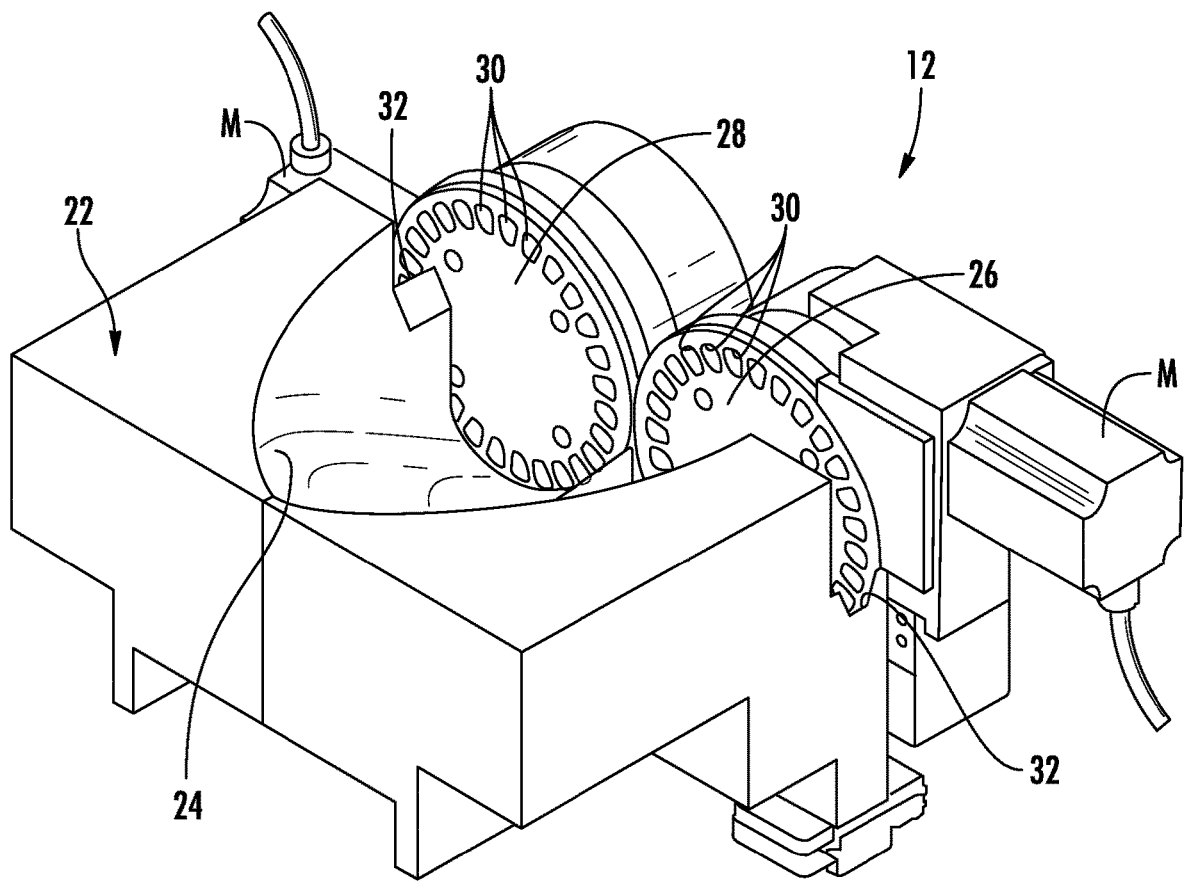
FIG. 2 is a perspective view of part of a seed loading assembly of the system of FIG. 1 illustrating a seed bin and a pair of separating wheels of the seed loading assembly.

With reference now to FIG. 2, the seed loading assembly 12 includes a seed bin 22 defining a reservoir 24 for receiving and holding seeds funneled from the seed hoppers 18, 20 (FIG. 1). The seed loading assembly 12 also includes two separating wheels 26, 28 operably mounted at least partially within the reservoir 24 (and in communication with seeds in the reservoir 24). Each of the separating wheels 26, 28 includes apertures 30 each in communication with a vacuum source (not shown). The apertures 30 (in conjunction with the vacuum source) are configured to capture individual seeds from the quantity of seeds in the reservoir 24 and retain the seeds in the apertures 30 as desired. Sensors may be disposed proximate to each of the separating wheels 26, 28 to, for example, sense whether individual seeds are captured correctly in the apertures 30 (e.g., one seed in one aperture 30, etc.), to count seeds as they enter the apertures 30 (e.g., as part of a quality control for monitoring the number of seeds entering the seed sampling system 10 and the number of seeds exiting the seed sampling system, etc.), combinations thereof, etc. And, agitators (e.g., mechanical mixers, air jets, vibratory devices, etc.) may be provided within the reservoir 24 to promote reception of seeds in the apertures 30 and help inhibit seeds from bridging (or forming voids), sticking, bunching, etc. at locations in the reservoir 24 where the apertures 30 receive seeds. In other example embodiments, sampling systems may include seed loading assemblies having more than or less than two separating wheels and/or separating wheels having different numbers and/or sizes of apertures therein.

Figure 3:
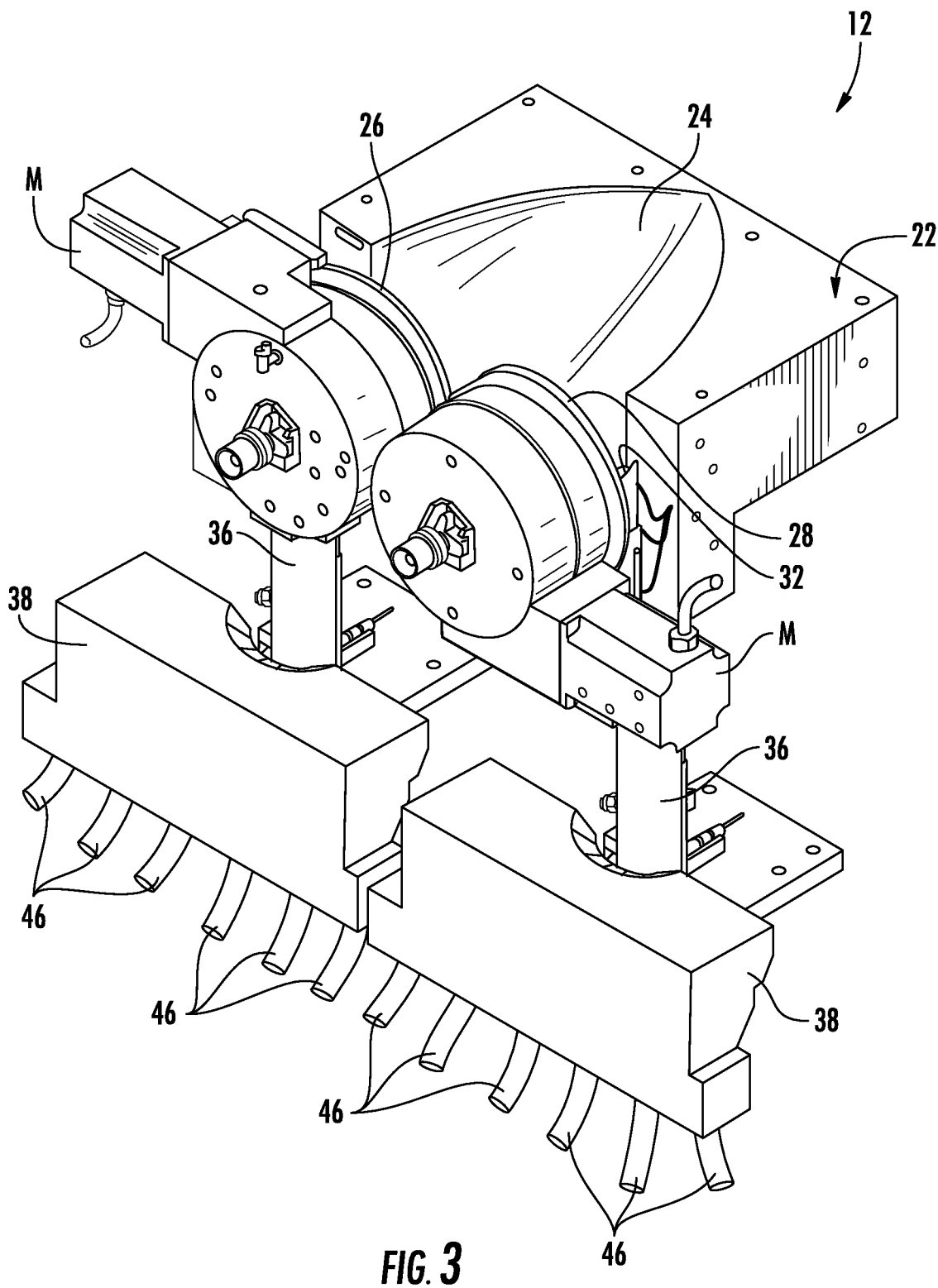
FIG. 3 is a perspective view of part of the seed loading assembly of the system of FIG. 1 illustrating the seed bin, the pair of separating wheels, a pair of diverters, and a pair of manifolds of the seed loading assembly.

In operation, the separating wheels 26, 28 rotate (operated by motors M) to move the apertures 30 through the reservoir 24 of the seed bin 22. In the illustrated embodiment, separating wheel 26 rotates in a different direction than separating wheel 28. For example, as viewed in FIG. 2, separating wheel 26 rotates in a clockwise direction and separating wheel 28 rotates in a counterclockwise direction. As each of the separating wheels 26, 28 rotates, suction is supplied to the apertures 30 (via the vacuum source) so that apertures 30 passing through the reservoir 24 capture and hold individual seeds within the apertures 30. As the separating wheels 26, 28 continue to rotate, they move the apertures 30 and captured seeds out of the reservoir 24 and to respective deposit compartments 32. In the deposit compartments 32, the captured seeds are dislodged from the apertures 30 (via reduced suction within the apertures 30 and/or wipers (not shown)) and received (e.g., via gravity, vacuum, etc.) in a transport chamber (not visible) extending through one of corresponding diverters 36 (FIG. 3). The separating wheels 26, 28 then continue to rotate and eventually move the emptied apertures 30 back into the reservoir 24 to capture additional seeds.

As shown in FIG. 3, the diverters 36 of the seed loading assembly 12 are disposed generally below the separating wheels 26, 28. The diverters 36 are each configured to individually distribute seeds dislodged from the separating wheels 26, 28 to a corresponding one of two manifolds 38. The diverters 36 may operate, for example, to rotate their transport chambers to select positions in alignment with one of multiple conduits (not visible) extending through the corresponding manifolds 38 and then transfer (e.g., via gravity, vacuum, mechanical operation, etc.) individual seeds from the transport chambers to the manifolds 38. More particularly, the diverters 36 may each operate to transfer an individual seed from its transfer chamber to one of the manifold conduits, and then rotate into alignment with another one of the manifold conduits and transfer another individual seed to that conduit. Sensors may be associated with the diverters 36 to, for example, sense received seeds, count seeds as they enter the diverters 36, combinations thereof, etc.

Figure 4:
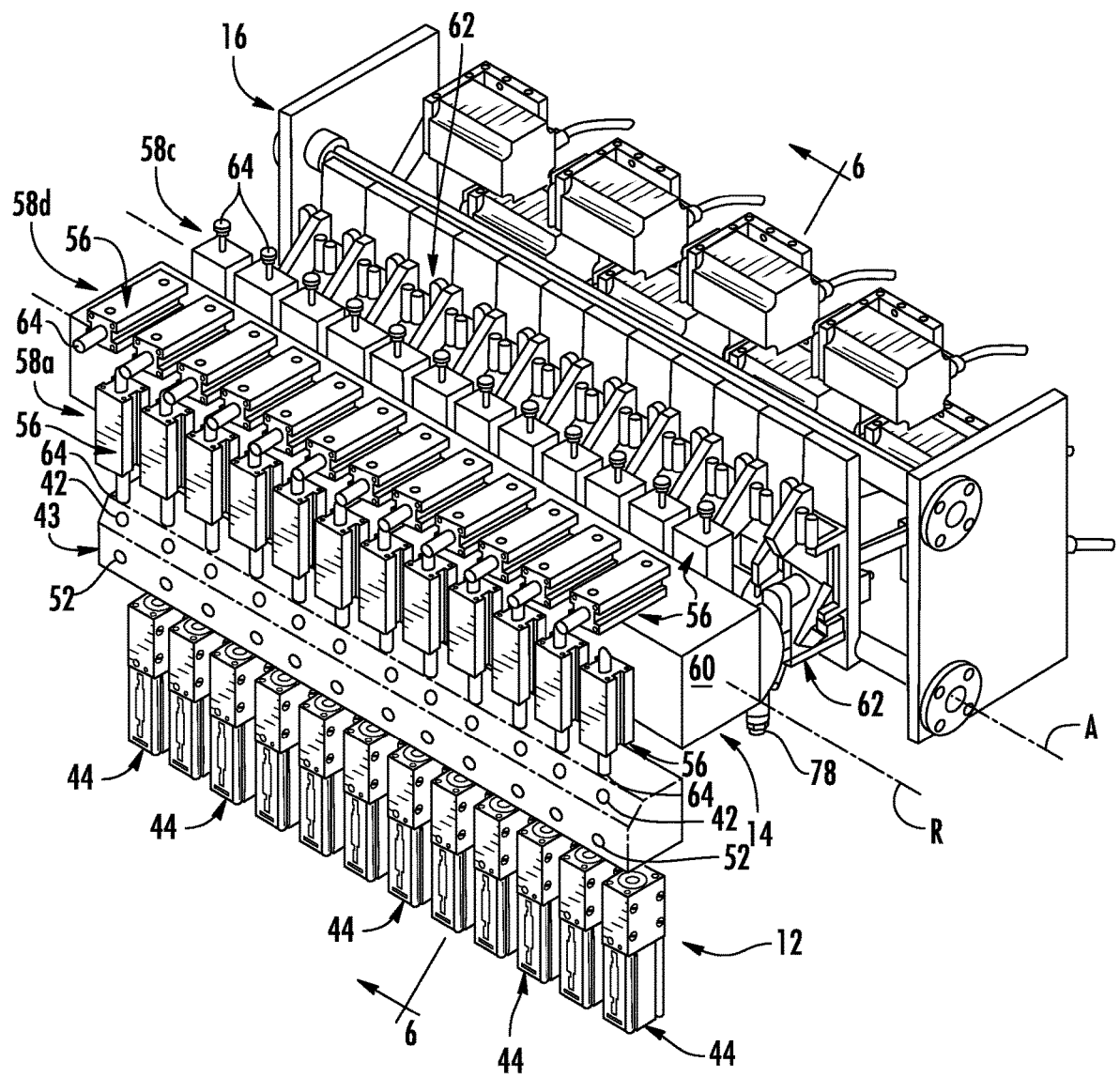
FIG. 4 is a perspective view illustrating operational relationship between part of the seed loading assembly, a seed transport assembly, and a seed sampling assembly of the system of FIG. 1.

As shown in FIG. 4, multiple elevator units 44 (e.g., twelve elevator units 44 in the illustrated embodiment, etc.) of the seed loading assembly 12 are positioned in a bank (or row) (generally below the diverters 36 (FIG. 3)) for receiving the singulated seeds from the manifolds 38 (FIG. 3). Each one of the elevator units 44 is in communication with one of multiple transport tubes 46 (FIG. 3) extending from a lower portion of each one of the manifolds 38. The transport tubes 46 couple to inlets 42 defined in an upper block portion 43 of the seed loading assembly with which each of the elevator units 44 are in communication. As such, singulated seeds from the manifolds 38 can be transferred (e.g., via gravity, vacuum, pressurized air, etc.) through the transport tubes 46, through the upper block portion 43, and to the elevator units 44 for subsequent transfer to the seed transport assembly 14.

Figure 5A:
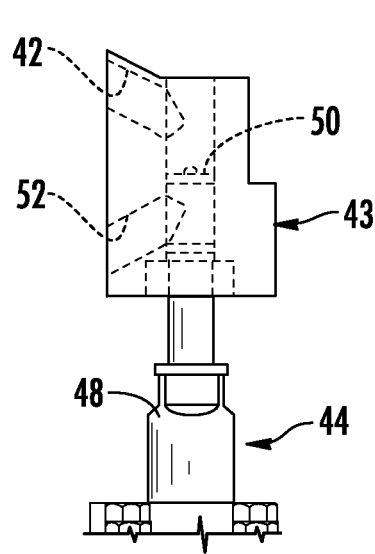
FIG. 5A is an elevation view of an example elevator unit of the seed loading assembly of FIG. 4 illustrating a piston of the elevator unit in a neutral position for receiving a singulated seed from one of the manifolds of the seed loading assembly.
Figure 5B:
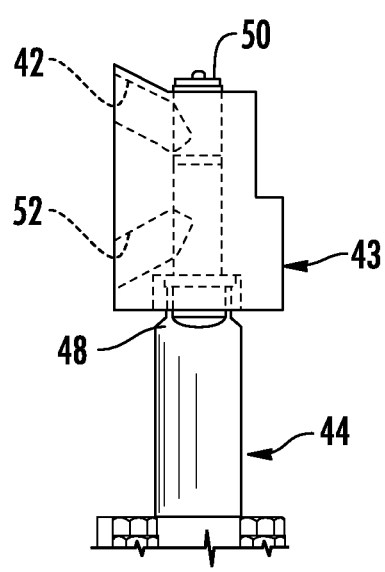
FIG. 5B is the elevation view of FIG. 5A with the piston of the elevator unit illustrated in an elevated position for transferring a singulated seed to the seed transport assembly.
Figure 5C:
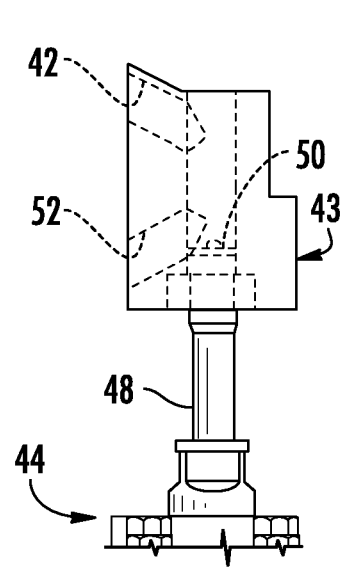
FIG. 5C is the elevation view of FIG. 5A with the piston of the elevator unit illustrated in a retracted position for expelling a singulated seed from the elevator unit.

With additional reference to FIGS. 5A-5C (illustrating an example elevator unit 44), the elevator units 44 each include pistons 48 movable (e.g., via pneumatic operation, etc.) between a neutral position (FIG. 5A), an elevated position (FIG. 5B), and a retracted position (FIG. 5C). When in the neutral position, each of the pistons 48 can receive seeds from the transport tubes 46 onto end portions 50 of the pistons 48. The pistons 48 are then configured to actuate the seeds from the neutral position to the elevated position for transfer/hand-off of the seeds to the seed transport assembly 14 (for subsequent transport to the seed sampling assembly 16). If necessary, the pistons 48 can also be actuated from either the neutral position or the elevated position to the retracted position where the seeds are exposed to an outlet 52 defined in the block portion 43 of the seed loading assembly 12 to expel the seeds (e.g., via gravity, vacuum, pressurized air, etc.), as desired, from the elevator units 44 (e.g., to a remnant bin, another location, etc.). The pistons 48 may be actuated to the retracted position, for example, if hand-offs are missed to the seed transport assembly 14, if multiple seeds are detected in one of the elevator units 44 at a given time, if seeds are detected having one or more specific characteristics (e.g., undesirable characteristics, particular sizes, particular types, etc. based on intermediate analysis, etc.), etc. Sensors may be associated with the elevator units 44 to, for example, sense seeds received from the manifolds 38, count seeds as they enter the diverters elevator units 44, evaluate seeds to be expelled, as desired, from the elevator units 44, combinations thereof, etc. In addition, end portions of the pistons 48 may include suction cups (e.g., vacuum cups, etc.) for use in receiving and retaining seeds (e.g., via negative pressure suction applied thereto, for example, through the pistons 48, etc.).

The separating wheels 26, 28 and diverters 36 of the seed loading assembly 12, in connection with the conduits in the manifolds 38, allow for singulation of individual seeds from the quantity of seeds originally funneled to the seed bin 22. As such, the seed loading assembly 12 operates to provide individual seeds to the seed transport assembly 14 for subsequent transfer to the seed sampling assembly 16. Sensors may also be disposed in communication with one or more of the diverters 36 (and their transport chambers), the manifolds 38 (and their conduits), and/or the transport tubes 46 to help further ensure that only one seed at a time is transferred through each of the transport tubes 46 to each of the elevator units 44 of the seed loading assembly 12.

With reference again to FIG. 4, the seed transport assembly 14 of the seed sampling system 10 is shown positioned adjacent the elevator units 44 of the seed loading assembly 12. And, the seed sampling assembly 16 is shown positioned adjacent the seed transport assembly 14. The seed transport assembly 14 includes multiple retention members 56 mounted in four banks 58a-58d about a generally tubular transport carousel 60 (e.g., four banks 58a-58d of twelve retention members 56 in the illustrated embodiment, etc.). And, the seed sampling assembly 16 includes multiple automated samplers 62 (e.g., twelve samplers 62 in the illustrated embodiment, etc.) generally aligned with the retention members 56. As can be seen, the illustrated embodiment includes the same number of elevator units 44, retention members 56 (in each of the banks 58a-58d), and samplers 62 such that the elevator units 44, retention members 56, and samplers 62 generally provide sampling paths through the seed sampling system 10 for the singulated seeds.

As will be described, retention members 56 of the seed transport assembly 14 operate to select (e.g., engage, retain, etc.) the singulated seeds from the corresponding elevator units 44 of the seed loading assembly 12 and then transfer the seeds to the corresponding samplers 62 of the seed sampling assembly 16 for sampling. In the illustrated embodiment, the transport carousel 60 is configured to rotate (e.g., via pneumatic operation, electric operation, etc.) the banks 58a-58d of elevator units 44 generally about rotational axis R (e.g., counter-clockwise as viewed in FIG. 4, etc.). The rotational axis R of the transport carousel 60 is generally parallel with a liner axis A defined by the multiple automated samplers 62, which are generally linearly disposed. In other example embodiments, systems may include seed transport assemblies having banks of retention members configured to rotate differently than disclosed herein, for example, about an axis that is substantially perpendicular to an axis generally defined by automated samplers thereof, etc.

The retention members 56 of the seed transport assembly 14 are configured to engage and receive seeds from the elevator units 44 (when the pistons 48 thereof actuate seeds to the elevated position) and transport the seeds to the samplers 62 of the seed sampling system 10. As previously described, the illustrated retention members 56 are organized into the four banks 58a-58d (only three of the banks 58a, 58c, 58d are visible in FIG. 4). The retention members 56 are generally evenly distributed along the transport carousel, and the banks 58a-58d are generally uniformly distributed around the transport carousel 60 (e.g., at about ninety-degree locations around the transport carousel 60, etc.). In other example embodiments, systems may include seed transport assemblies having more than or fewer than four banks of retention members and/or banks of retention members oriented differently than disclosed herein.

Figure 6:
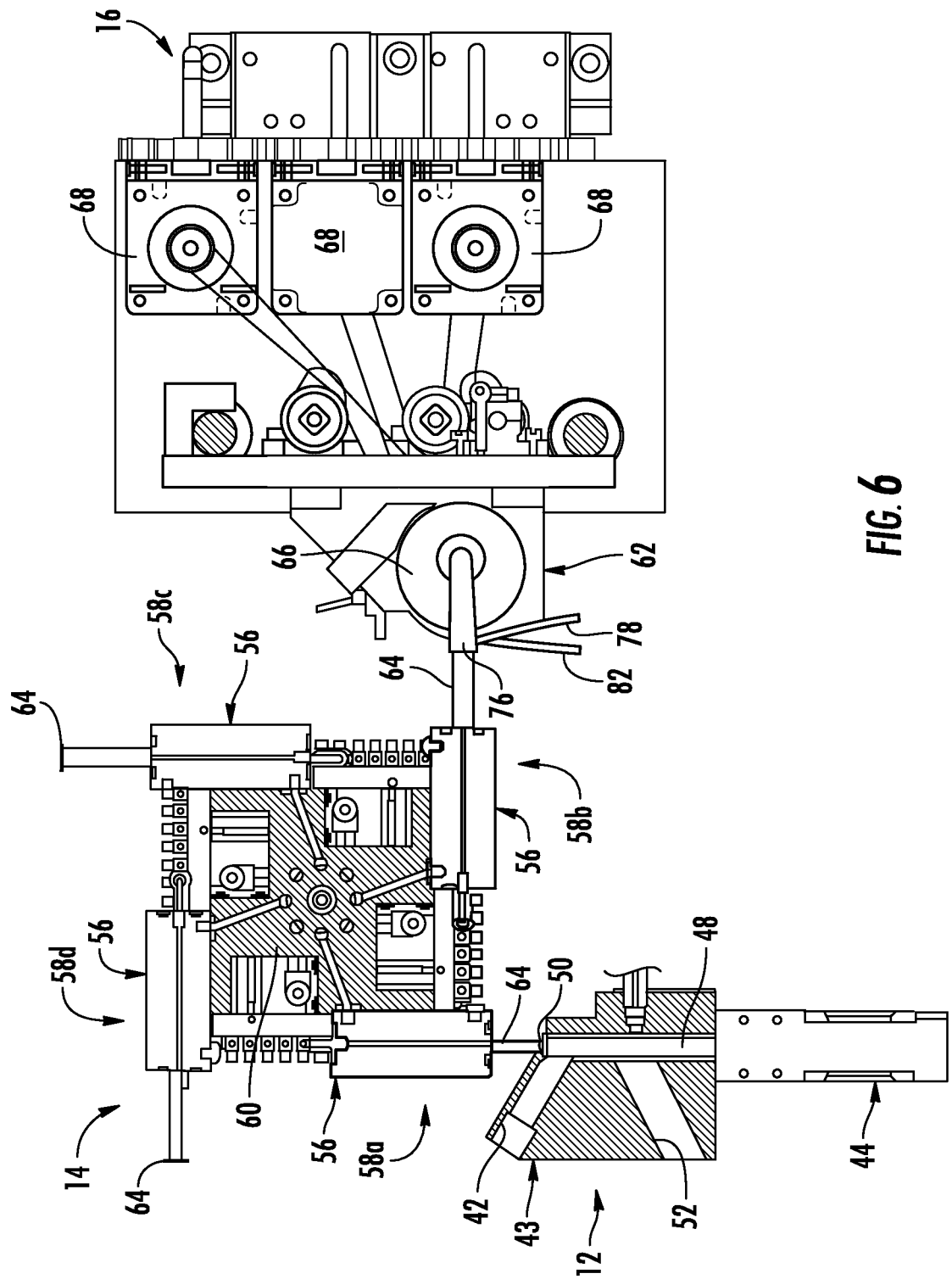
FIG. 6 is a section view of part of the seed loading assembly, the seed transport assembly, and the seed sampling assembly taken in a plane including line 6-6 in FIG. 4.

With additional reference to FIG. 6, bank 58a of retention members 56 is shown positioned adjacent to the elevator units 44 for receiving seeds while bank 58c is positioned adjacent to the samplers 62 of the seed sampling assembly 16 for presenting seeds to the samplers 62 for sampling. And, banks 58b and 58d are shown at idle positions between the seed loading assembly 12 and the seed sampling assembly 16. Bank 58b includes a seed shown in transport to the seed sampling assembly 16, and bank 58d is empty. After the seeds presented to the samplers 62 by the retention members 56 of bank 58c are sampled, the retention members 56 release the seeds for subsequent transport as will be described hereinafter. The transport carousel 60 then rotates counter-clockwise (as viewed in FIG. 6) (i.e., through an angle of about ninety degrees) to position bank 58b adjacent to the samplers 62 (for presenting their seeds to the samplers 62), and bank 58d rotates to a position adjacent the elevator units 44 (for receiving additional seeds). Banks 58a and 58c are rotated to the idle positions, with each of the retention members 56 in bank 58a retaining a seed. The seed transport assembly 14 is operable to continuously rotate the banks 58a-58d of the retention members 56 between the elevator units 44 and the automated samplers 62.

The retention members 56 include end portions 64 configured to retain the seeds received from the elevator units 44. In the illustrated embodiment, the end portions 64 include suction cups (e.g., vacuum cups, etc.) for use in receiving and retaining seeds (e.g., via negative pressure suction, etc.). The suction cups may include cup-shaped end portions, defining, for example, V-shapes, U-shapes, other shapes, etc. conducive to holding seeds The suction cups are configured such that when air pressure is supplied to the suction cups, seeds can be engaged and retained thereby (with one seed received in one suction cup). In addition, the suction cup end portions 64 of the retention members 56 are movable (e.g., via pistons, etc.) relative to the transport carousel 60 (and the seed sampling system 10) for positioning seeds in the samplers 62 of the seed sampling system 10. In this manner, when the retention members 56 are rotated to positions adjacent to samplers 62, the suction cup end portions 64 may be actuated (e.g., via pistons, etc.) toward the samplers 62 (relative to the transport carousel 60) to present the seeds for sampling. In other example embodiments, systems may include seed transport assembly having retention members with end portions defining other than suction cups for use in receiving and retaining seeds, for example, mechanical holders, seed gripping mechanisms, etc.

Figure 7:
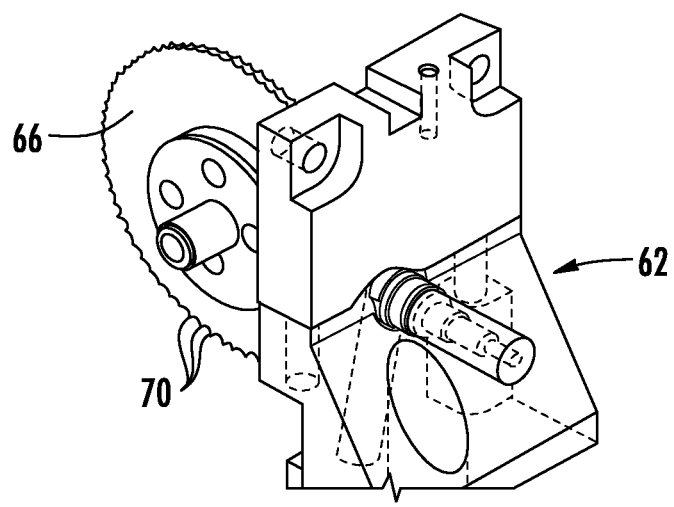
FIG. 7 is a perspective view of an example sampler of the seed sampling assembly of FIG. 4.
Figure 8:
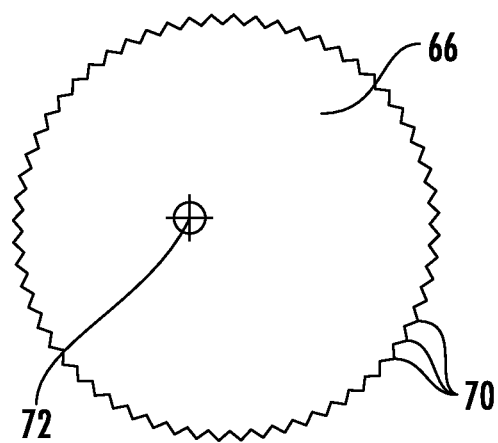
FIG. 8 is an elevation view of a cutting wheel of the sampler of FIG. 7.
Figure 10:
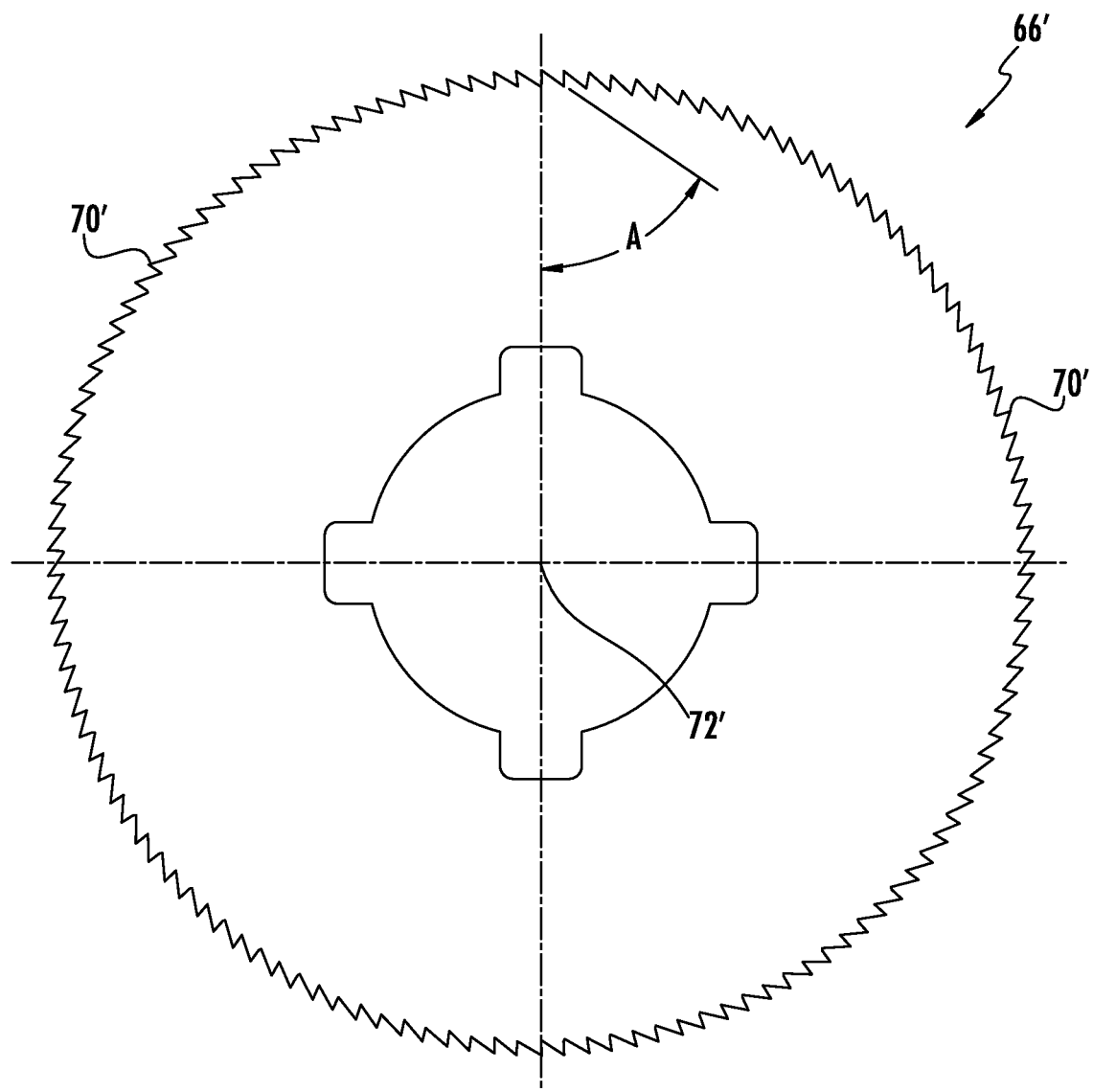
FIG. 10 is an elevation view of another example embodiment of a cutting wheel suitable for use, for example, with the sampler of FIG. 7.

With reference now to FIGS. 7 and 8, the samplers 62 of the seed sampling assembly 16 each include a cutting wheel 66 operably coupled to a motor 68 (FIG. 6) for rotating the cutting wheel 66 during operation. The illustrated cutting wheel 66 includes teeth 70 configured to remove a tissue sample from a seed. The cutting wheel 66 is configured to rotate about an off-center axis 72 during operation. This allows each tooth 70 of the cutting wheel 66 to take a different rotational path into the seed (depth wise) such that each tooth 70 removes a different portion of tissue from the seed, at locations progressively, incrementally, etc. deeper in the seed. FIG. 10 illustrates another example embodiment of a cutting wheel 66' that could be used with the samplers 62 of the seed sampling assembly 16. In this embodiment, the cutting wheel 66' is configured to rotate about a generally central axis 72'. And, the cutting wheel 66' includes teeth 70 (e.g., about 130 total teeth 70, etc.) each oriented at an angle A (e.g., at an angle A of about 57 degrees, etc.). In other example embodiments, systems may include automated samplers having features other than cutting wheels for removing tissue samples from seeds, for example, broaches, lasers, knives, etc.

Figure 9:
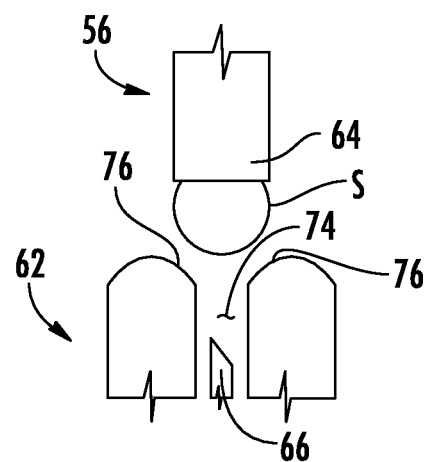
FIG. 9 is a schematic illustrating positioning of a singulated seed by a retention member of the seed transport assembly of FIG. 4 adjacent a sampler of the seed sampling assembly of FIG. 4 for removing a tissue sample from the singulated seed.

With additional reference to the schematic in FIG. 9, the samplers 62 also each define a channel 74 adjacent the cutting wheel 66 for guiding movement (e.g., orienting, etc.) of seeds into a desired position (orientation, etc.) within the samplers 62 (i.e., adjacent the cutting wheel 66). As shown in the example sampler 62, the channel 74 is defined by two ramp surfaces 76 configured to direct (e.g., deflect, etc.) a seed, as needed, into the desired position adjacent the cutting wheel 66. When the end portion 64 of the retention member 56 (retaining the seed S) is actuated toward the automated sampler 62, the ramp surfaces 76 guide the seed S into the desired position. The end portion 64 of the retention member 56 may comprise a flexible material (e.g., rubber, etc.) so that the end portion 64 can be actuated (e.g., deflected, etc.) as needed to position the seed S in the desired position between the ramp surfaces 76. Sensors may be associated with the samplers 62 to, for example, sense received seeds, count seeds as they enter the samplers 62 from the retention members 56, combinations thereof, etc.

The size and/or shape of the tissue sample removed by the cutting wheels 66 may be adjusted as desired (e.g., based on seed size, seed type, sample testing, etc.). For example, the seed sampling system 10 may adjust the size/shape of a tissue sample by controlling each of the samplers 62 independently, or alternatively, by controlling any two or more of the samplers 62 uniformly. Further, the samplers 62 may control the position and/or rotation of the cutting wheels 66, based on when seeds are presented to the samplers 62, to ensure incremental removal of tissue samples from the seeds. For example, one or more of the cutting wheels 66 may be stationary when seeds are presented to the samplers 62, then subsequently rotated to remove tissue samples from the seeds. Alternatively, one or more of the cutting wheels 66 of the automated samplers 62 may be rotating when the seeds are presented.

Referring again to FIG. 6, after the tissue samples are removed from the seeds, the sampled seeds are captured (e.g., released from the retention members 56 of the seed transport assembly 14 and funneled, etc.) and transported through conduits 78 (e.g., via gravity, air pressure, air jets, etc.) to a seed tray 80 (FIG. 1). And, the tissue samples are captured (e.g., funneled, etc.) and transported through conduits 82 (e.g., via gravity, air pressure, air jets, etc.) to a sample tray (not shown). The seed tray 80 may include multiple wells (e.g., ninety-six, three hundred eighty-four, etc.), and the sample tray may include multiple corresponding wells. In addition, the seed tray 80 may include the same number of wells as the sample tray, or a different number (e.g., a multiple thereof, etc.) within the present disclosure. The seeds are deposited in wells of the seed tray 80, and the tissue samples from the seeds are deposited in one or more corresponding wells of the sample tray. As such, the seeds and the tissue samples taken from the seeds may be subsequently correlated. Sensors may be positioned (e.g., along conduits 78, 82, etc.) to, for example, sense, count, etc. sampled seeds and/or tissue samples received in the sample tray and/or the seed tray 80.

Seed and sample trays may be positioned and/or controlled via one or more stages (not shown) movable in the X-Y directions or otherwise, to position the trays relative to conduits (e.g., conduits 78, 82, etc.) to ensure the seeds and the tissue samples are deposited in wells of the trays. Additionally, or alternatively, conduits may be structured and/or operable to ensure tissue samples and seeds are deposited, as desired, without cross-contamination with other tissue samples/seeds. Additionally, or alternatively, sample trays may be sealed, via covers, etc., prior to or just after removal of sample trays from sampling systems to limit cross-contamination of tissue samples retained in each well of the sample trays. Seed trays may be similarly sealed to retain seeds in their respective wells.

In the illustrated embodiment, the engagement of seeds by the retention members 56 at the elevator units 44 and the sampling of seeds at the automated samplers 62 may occur substantially simultaneously, thereby increasing throughput of the system 10. For example, the throughput-rate (e.g., output of sampled seeds, etc.) of the illustrated seed sampling system 10 is at least about four seeds per second (e.g., between about four and about six seeds per second, etc.). As such, the seed sampling system 10 may be viewed as a high-throughput system, etc. It should be appreciated that different numbers of elevator units, retention members, and/or samplers as well as different numbers of banks of retention members may be provided to adjust the throughput rate as desired. Additionally, positioning of one or more of the components may be modified (e.g., locations of the banks of retention members, etc.) to adjust the throughput rate of the automated seed sampling system.

FIGS. 11-16 illustrate another example embodiment of an automated seed sampling system 110 including one or more aspects of the present disclosure. The system 110 of this embodiment is again suitable for use in removing samples from biological materials, and is substantially similar to the seed sampling system 10 previously described and illustrated in FIGS. 1-9. In fact, the parts previously described for the seed sampling system 10 can readily be used in connection with the system 110 of this embodiment, and vice versa.

Figure 11:
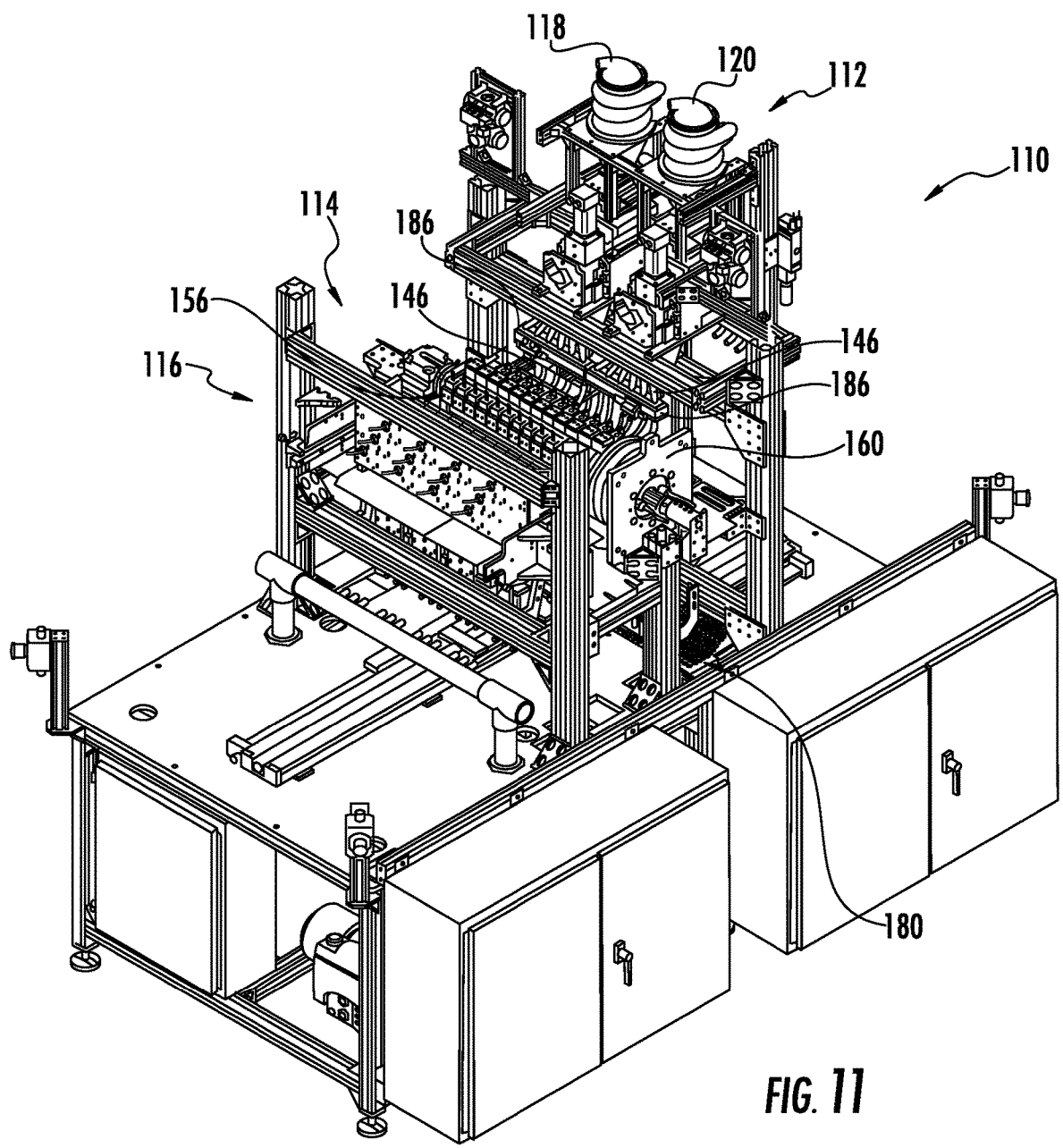
FIG. 11 is a perspective view of another example embodiment of a seed sampling system including one or more aspects of the present disclosure and configured to singulate seeds and remove tissue samples from the singulated seeds.
Figure 12:
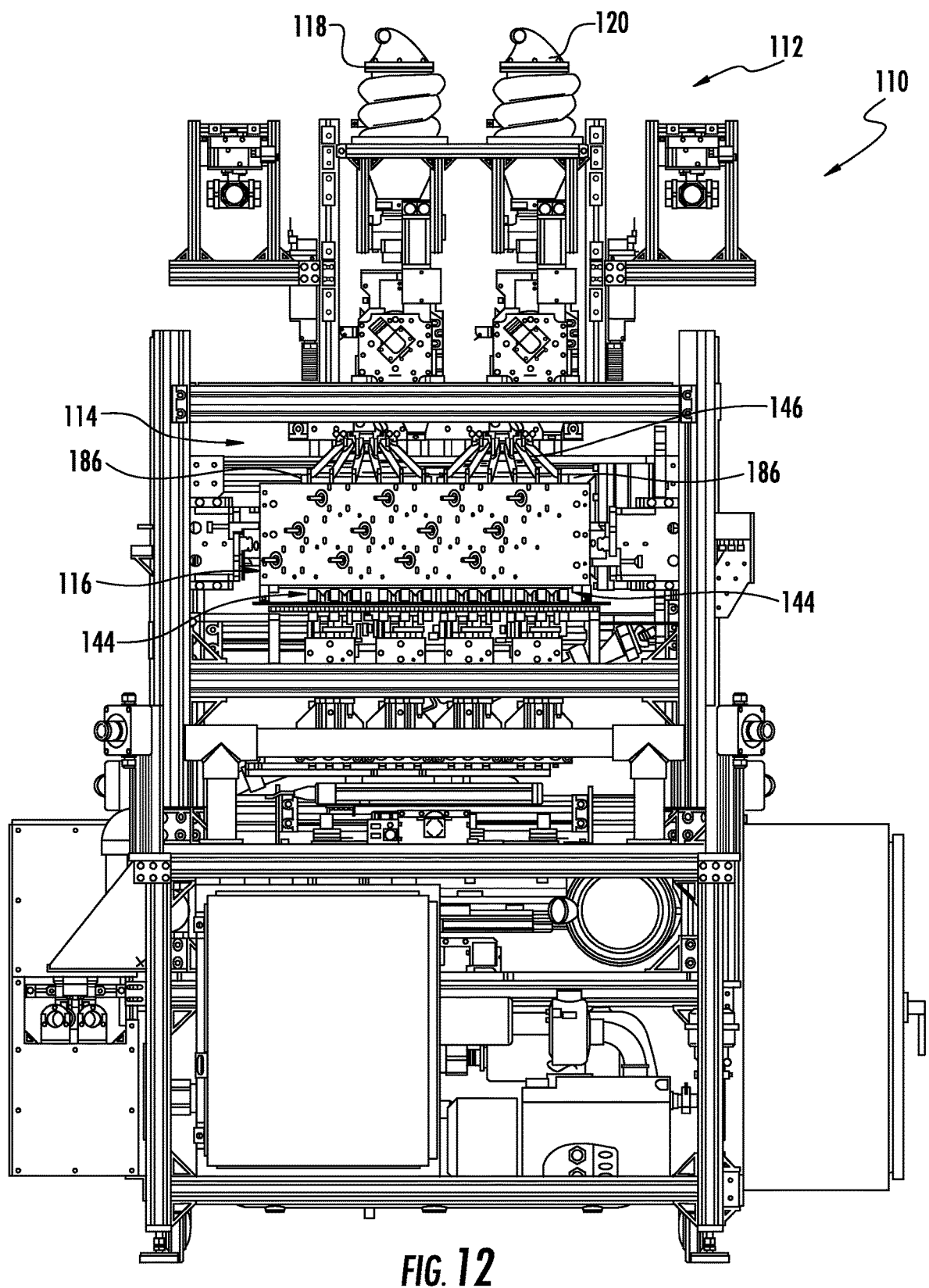
FIG. 12 is an end elevation view of the seed sampling system of FIG. 11.
Figure 13:
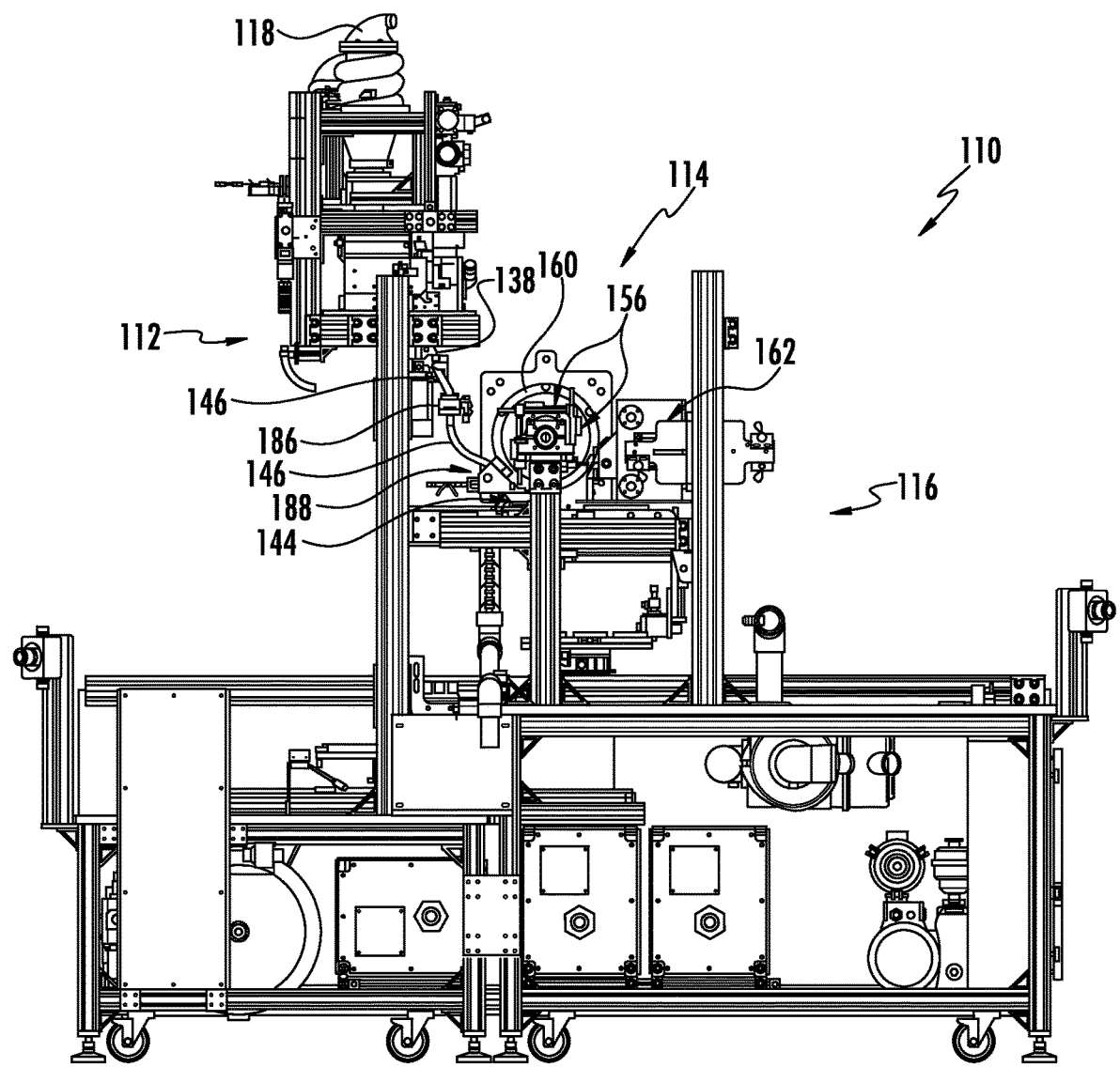
FIG. 13 is a side elevation view of the seed sampling system of FIG. 11.

As shown in FIGS. 11-13, the seed sampling system 110 generally includes an automated seed loading assembly 112, an automated seed transport assembly 114, and an automated seed sampling assembly 116. And, the seed loading assembly 112, the seed transport assembly 114, and the seed sampling assembly 116 are substantially similar to (and operate in substantially similar manners to) the corresponding assemblies 12, 14, 16 of the seed sampling system 10. As such, the prior descriptions of the seed loading assembly 12, the seed transport assembly 14, and the seed sampling assembly 16 similarly apply hereto.

For example, seed hoppers 118, 120 are provided for receiving quantities of seeds into the sampling system 110 and for directing the seeds to the seed loading assembly 112, which then operates to singulate (or isolate, etc.) individual seeds received from the hoppers 118, 120. The seed loading assembly 112 includes a seed bin (not visible) for receiving and holding seeds funneled from the seed hoppers 118, 120. And, separating wheels (not visible) operate to singulate individual seeds from the seed bin for transport to one of two manifolds 138 (FIG. 13) which, in turn, then distribute the singulated seeds to one of multiple elevator units 144 (e.g., twelve elevator units 144 in the illustrated embodiment, etc.) for subsequent transfer to the seed transport assembly 114.

Also for example, the seed transport assembly 114 operates to move the singulated seeds from the loading assembly 112 to the seed sampling assembly 116 where tissue samples are removed from the seeds. The seed transport assembly 114 includes multiple retention members 156 mounted in four banks about a generally tubular transport carousel 160 (e.g., four banks of twelve retention members 156 in the illustrated embodiment, etc.). The retention members 156 operate to select (e.g., engage, retain, etc.) the singulated seeds (e.g., via suction cups, etc.) from the corresponding elevator units 144 and transfer the seeds (via rotation of the transport carousel 160) to the seed sampling assembly 116. And, the seed sampling assembly 116 includes multiple automated samplers 162 (FIG. 13) (e.g., twelve samplers 162 in the illustrated embodiment matching the number of retention members 156 in each bank, etc.) generally aligned with the retention members 156 for sampling the seeds held in the retention members 156. The sampled seeds are then received in a seed tray 180 (e.g., the seeds are released from the retention members 156 and directed to the seed tray 180, etc.), and the tissue samples are received in a sample tray (not shown) (e.g., the tissue samples are directed to the sample tray, etc.).

In this embodiment (and as compared to the seed sampling system 10), the seed loading assembly 112 further includes two sensors 186 positioned generally below the two manifolds 138 (FIG. 13) and a bank (or row) of multiple orientation units 188 (e.g., twelve orientation units 188 in the illustrated embodiment matching the number of retention members 156 in each bank of the seed transport assembly 114 and the number of samplers 162 of the seed sampling assembly 116, etc.) positioned generally below the two sensors 186 and adjacent the elevator units 144. The sensors 186 and the orientation units 188 are in communication with multiple transport tubes 146 extending from a lower portion of each one of the manifolds 138. The transport tubes 146 extend from the lower portion of the manifolds 138, through the sensors 186, and couple to inlets 142 (see FIGS. 14-16) defined in upper portions of the orientation units 188. As such, in this embodiment singulated seeds from the manifolds 138 are first transferred by the transport tubes 146 (e.g., via gravity, vacuum, pressurized air, etc.) through the sensors 186 and to the orientation units 188, and then are transferred from the orientation units 188 to the elevator units 144 for subsequent presentation to the seed transport assembly 114.

The orientation units 188 are configured to orient the singulated seeds prior to transfer of the seeds to the seed transport assembly 114. As such, also in this embodiment, the seed transport assembly 114 operates to transport the singulated seeds in particular orientations to the seed sampling assembly 116 (e.g., such that tissue samples can be taken from particular portions of the oriented seeds, such that the seeds can be more securely transferred by the retention members 156, etc.). In connection with this operation of the seed sampling system 110, the sensors 186 are configured to sense if the singulated seeds are transferred from the manifolds 138 to the orientation units 188 (e.g., as part of a quality control program, to initiate operation of the orientation units, etc.). The sensors 186 may also (or alternatively) be configured to, for example, count the number of seeds transferred from the manifolds 138 to the orientation units 188, etc. Any suitable sensors may be used for these operations within the scope of the present disclosure.

Figure 14:
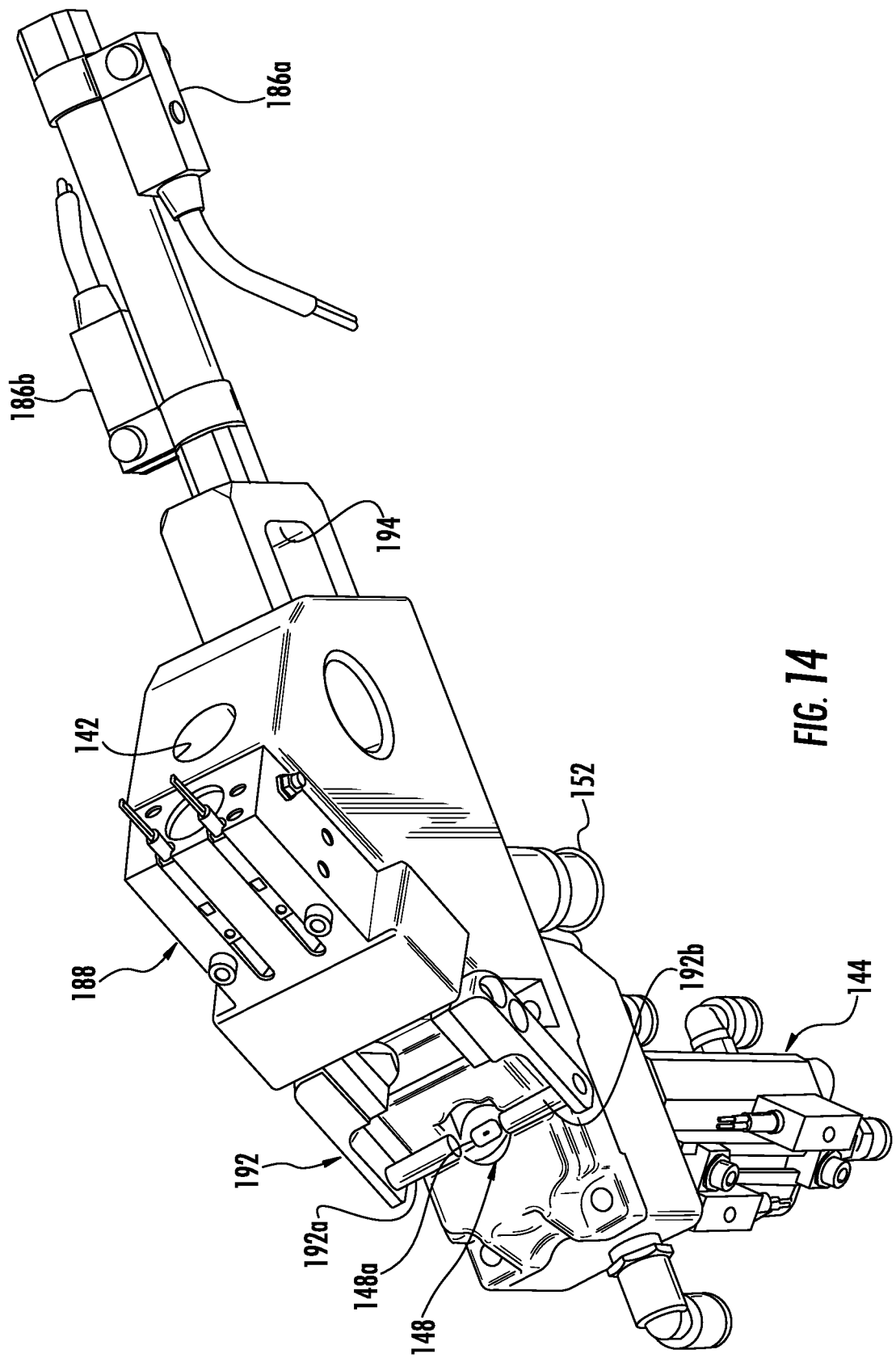
FIG. 14 is a perspective view of an example orientation assembly of the seed sampling system of FIG. 11 operable to orient singulate seeds prior to operation of the seed sampling system to remove tissue samples from the seeds.
Figure 15:
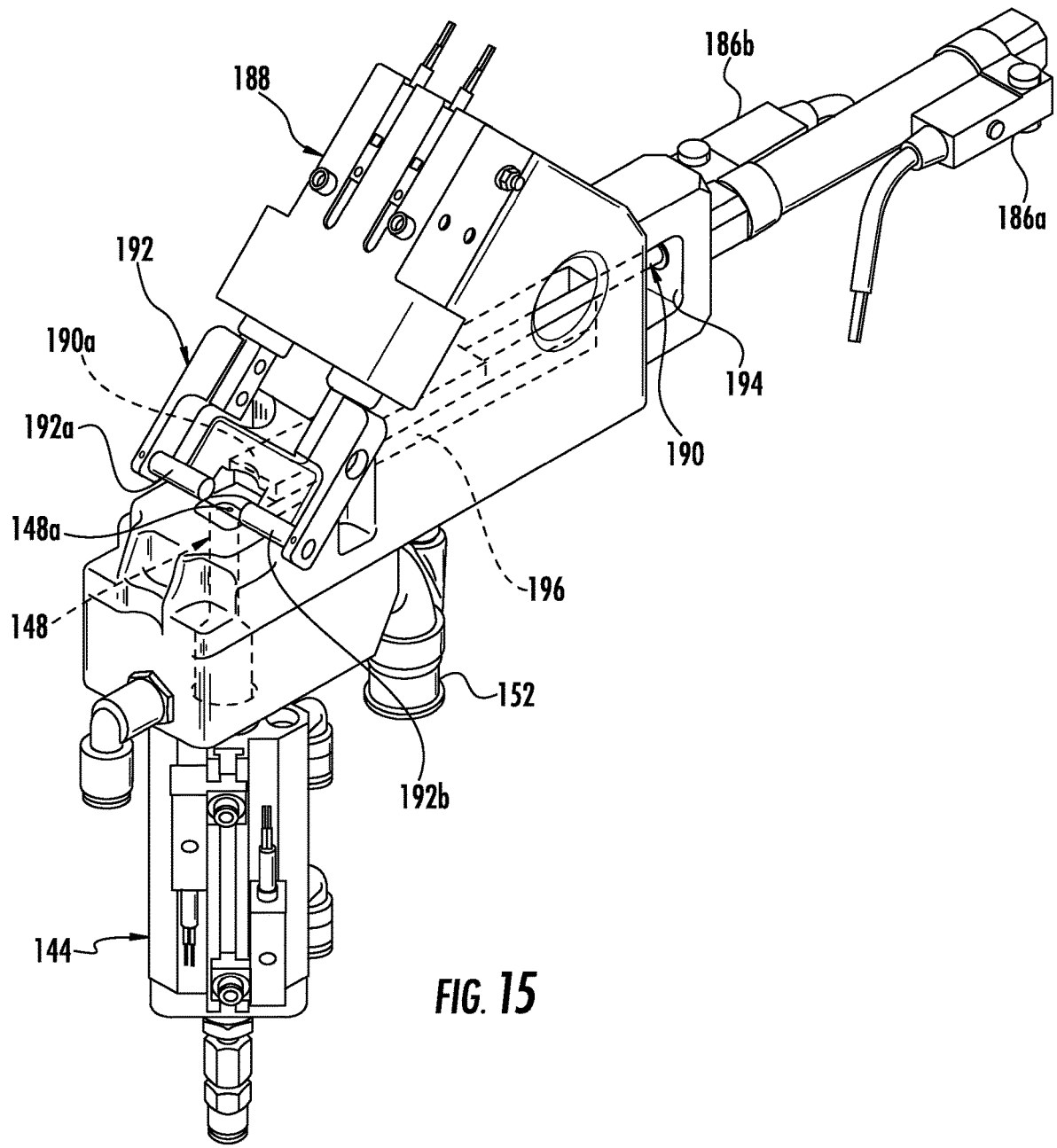
FIG. 15 is another perspective view of the orientation assembly of FIG. 14.
Figure 16:
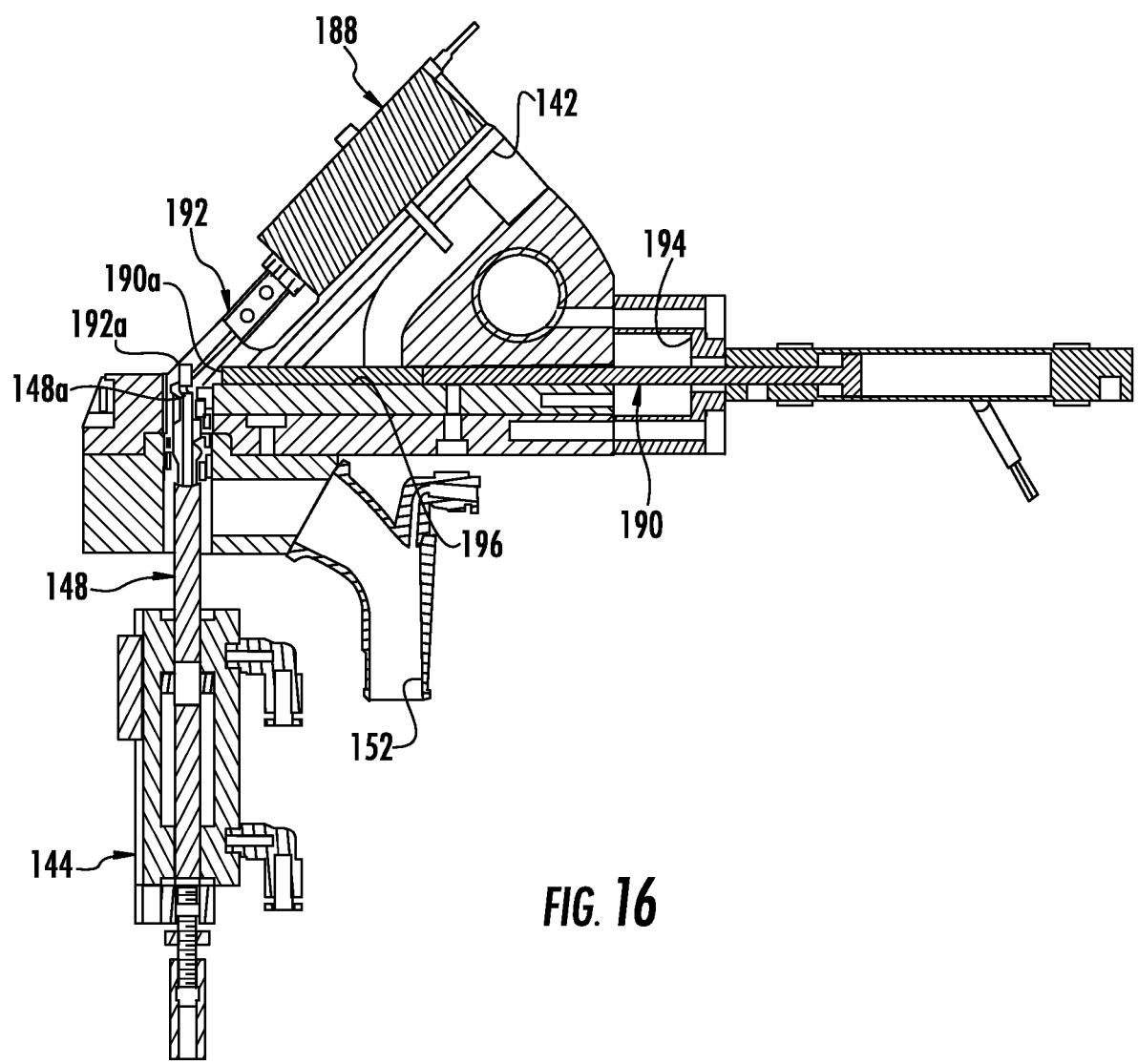
FIG. 16 is a longitudinal section view of the orientation assembly of FIG. 14.

FIGS. 14-16 illustrate an example one of the orientation units 188 of the seed loading assembly 112 together with an example one of the elevator units 144 of the assembly 112. The illustrated orientation unit 188 generally includes an actuator 190 configured to orient a singulated seed and a support 192 configured to receive the oriented seed from the actuator 190 in preparation for transfer to the elevator unit 144. A transport tube 146 (not shown in FIGS. 14-16) couples to the inlet 142 of the orientation unit 188 for transferring a singulated seed from one of the two manifolds 138 to the orientation unit 188. The elevator unit 144 is located generally below the support 192. In this position, a piston 148 of the elevator unit 144 (shown in a neutral position in FIGS. 14-16) can engage the oriented seed located in the support 192 for subsequent presentation of the seed to the seed transport assembly 114 (as previously described in connection with the seed sampling assembly 10 illustrated in FIGS. 1-9).

In the illustrated embodiment, the actuator 190 of the orientation unit 188 moves the received seed to orient the seed. The actuator 190 is movable (e.g., via pneumatic operation, etc.) between a retracted position for receiving a singulated seed and an extended position for orienting the received seed and transferring it to the support 192. Sensor 186a is provided for sensing when the actuator 190 is in the refracted position, and sensor 186b is provided for sensing when the actuator 190 is in the extended position. In the retracted position a head portion 190a of the actuator is located toward a recess 194 of the orientation unit 188 such that a singulated seed can be received from the inlet 142 and onto a guide surface 196 of the orientation unit 188, generally between the head portion 190a and the support 192. Movement of the actuator 190 from the refracted position to the extended position then pushes the received seed along the guide surface 196 toward the support 192, causing the seed to roll/tumble until a generally broad surface (e.g., a generally flat surface, a generally wider one of the surfaces, etc.) of the seed orients along the guide surface 196. The actuator 190 then slides the seed in this orientation (along the seed's generally broad surface) to the support 192 and generally over the piston 148 of the elevator unit 144 (with the generally broad surface of the seed facing an end portion 148a of the piston 148).

Once the oriented seed is received in the support 192, the support 192 operates to help hold the oriented seed over the piston 148 of the elevator unit 144. For example, arms 192a, 192b of the support 192 frictionally engage the seed to help hold the seed in its oriented position over the end portion 148a of the piston 148. In addition, the support 192 may operate to sense (e.g., via a suitable sensors, etc.) if the seed is in a particular, desired orientation (e.g., an orientation with the generally broad surface of the seed facing the end portion 148a of the piston 148, etc.).

The elevator unit 144 then operates the piston 148 from the neutral position to engage and receive the seed on the end portion 148a of the piston 148. In this embodiment, the end portion 148a of the piston 148 includes a vacuum cup for receiving and holding the seed (e.g., via negative pressure suction applied thereto, for example, through the piston 148, etc.) on the end portion 148a of the piston 148. The elevator unit 144 can then move to either an elevated position for transfer/hand-off of the seed to a retention member 156 of the seed transport assembly 114 (for subsequent transport to the seed sampling assembly 116) or a refracted position for expelling the seed (e.g., via gravity, vacuum, pressurized air, etc.) from the elevator unit 144 (via outlet 152 between the elevator unit 144 and the orientation unit 188). For example, as previously described a desired orientation of the seed may include one in which the generally broad surface of the seed is engaged by the end portion 148a of the piston 148. Here, if the seed is in the desired orientation in the support 192 (e.g., as determined by the sensing feature of the support 192, etc.), the elevator unit 144 will move the oriented seed to the elevated position and the retention member 156 will engage the oriented seed along a surface opposite the seed's generally broad surface. Thus, upon transfer of the oriented seed to the seed sampling assembly 116, a tissue sample will be removed from the generally broad surface of the seed. Alternatively, if the seed is not in the desired orientation, the elevator unit 144 will move the seed to the retracted position and the seed will be expelled from the seed sampling system 110 through the outlet 152.

The seed sampling system 110 of this embodiment can be used to sample any desired type of seed. However, it may be particularly useful for sampling wheat seeds which may be generally D-shaped or generally triangular-shaped and which typically have generally broader (e.g., generally flat, etc.) surfaces located opposite the embryos of the seeds. As such, the orientation units 188 can orient the wheat seeds prior to sampling (prior to using the samplers 162 to remove tissue samples from the wheat seeds) so that tissue samples are removed from the wheat seeds at locations away from the embryos (e.g., at locations along the generally broader surfaces of the wheat seeds, etc.), for example, to help preserve germination viability of the wheat seeds, etc.

In some example embodiments, systems (e.g., system 10, system 110, etc.) may include additional assemblies for imaging and/or orienting seeds (e.g., in addition to orientation unit 188, other than orientation unit 188, etc.). For example, seeds may be imaged and/or oriented prior to and/or after presentation to sampling stations. In at least one embodiment, a seed sampling system includes a camera (or other imaging device) to image a seed, prior to sampling, so that samplers are able to utilize the size, shape, other characteristics, etc. of the seeds to appropriately position the seeds and/or samplers (e.g., cutting wheels, etc.) so that desired tissue samples are removed from the seeds. Example systems and/or methods suitable for imaging and/or orienting seeds are disclosed in U.S. Patent Application Publications 2007/0207485 and 2008/0317279 (the disclosures of which are hereby incorporated by reference in their entireties).

For example, seed sampling system 110 may include an imaging device (e.g., a camera, etc.) operable in connection with the orientation unit 188 or, alternatively, operable in place of the orientation unit. Here, the imaging device is configured to image a seed, prior to sampling, so that samplers are able to utilize the size, shape, other characteristics, etc. of the seeds to appropriately position the seeds and/or samplers (e.g., cutting wheels, etc.) so that desired tissue samples are removed from the seeds. This can be used, for example, to orient the seeds in desired positions prior to sample, to help analyze the seeds after sampling, as part of a quality control program to monitor operation of the seed sampling system 110 (e.g., to help adjust (e.g., speed up, slow down, etc.) various processes (e.g., processes of the seed loading assembly 112, the seed transport assembly 114, the seed sampling assembly 116, etc.) of the seed sampling system 110 during operation and without interrupting the processes, etc.), etc. The various sensors included in the seed sampling system 10 and seed sampling system 110 can similarly be used, for example, to help analyze the seeds after sampling, as part of a quality control program to monitor operation of the seed sampling systems 10, 110, etc.

In some example embodiments, seed sampling systems may include seed loading assemblies having seed hopper units provided for receiving seeds into the sampling systems and for directing the seeds to the seed loading assemblies. In these embodiments, the seed hopper units may each be configured (e.g., sized, shaped, constructed, etc.) to singulate seeds (e.g., via separating wheels in each of the hopper units, etc.) and direct the singulated seeds to corresponding manifolds (such that each of the hopper units process a separate stream of seeds).

Seed sampling systems (e.g., system 10, system 110, etc.) and methods of the present disclosure are operable to protect, preserve, etc. germination viability of sampled seeds and thus may, for example, be considered non-destructive. For example, the size, position and/or shape of the tissue samples removed may be controlled precisely to protect germination viability of the sampled seeds. Germination viability means that a predominant number of sampled seeds, (i.e., greater than about 50% of all sampled seeds) remain viable after sampling. In a particular embodiment, at least about 75% of sampled seeds, and in some embodiments at least about 85% of sampled seeds remain viable. It should be noted that lower rates of germination viability may be tolerable under certain circumstances or for certain applications, for example, as genotyping costs decrease with time because a greater number of seeds could be sampled for the same genotype cost. It should also be noted that sampling does not need to have any effect on viability at all.

In one embodiment, germination viability of the sampled seeds is maintained for at least about six months after sampling to ensure that the sampled seeds will be viable until they reach the field for planting. In a particular embodiment, the sampled seeds are further treated to maintain germination viability. Such treatment may generally include any means known in the art for protecting a seed from environmental conditions while in storage or transport. For example, in one embodiment, the sampled seeds may be treated with a polymer and/or a fungicide to protect the sampled seed while in storage or in transport to the field before planting.

Seed sampling systems (e.g., system 10, system 110, etc.) of the present disclosure may define generally compact footprints. For example, a system (e.g., seed sampling system 10, seed sampling system 110, etc.) having a seed loading assembly with twelve elevator units, a seed transport assembly with four banks of twelve retention members, and a seed sampling assembly with twelve samplers may define a foot print of about ten feet by about ten feet, and may have a height of about eight feet. Such a foot print is permitted by the configurations of the seed loading assembly, the seed transport assembly, and/or the seed sampling assembly of the system. The compact footprint (and compact size) permits the system to be transported for operation at different locations. Systems having seed loading assemblies with other than twelve elevator units, seed transport assemblies with other than four banks of twelve retention members, and seed sampling assemblies with other than twelve samplers may define other foot prints within the scope of the present disclosure.

Seed sampling systems (e.g., system 10, system 110, etc.) of the present disclosure are configured to accommodate different types of seeds and/or different sizes of seeds. For example, apertures of separating wheels may be configured to accommodate individual ones of different types and/or sizes of seeds (e.g., via brushes to automatically adjust for variability in seed sizes, etc.) so that the sampling systems can be used to process different types of seeds without changing the separating wheels. In addition, end portions of retention members may be configured to retain individual ones of different types and/or sizes of seeds. And, samplers may be configured to sample individual ones of different types and/or sizes of seeds.

Example seeds that could be used with the seed sampling systems (e.g., system 10, system 110, etc.) and methods of the present disclosure include alfalfa seed, apple seed, banana seed, barley seed, bean seed, broccoli seed, cabbage seed, canola seed, carrot seed, castorbean seed, cauliflower seed, Chinese cabbage seed, citrus seed, clover seed, coconut seed, coffee seed, maize seed, cotton seed, cucumber seed, Douglas fir seed, dry bean seed, eggplant seed, Eucalyptus seed, fennel seed, garden bean seed, gourd seed, leek seed, lettuce seed, Loblolly pine seed, linseed seed, melon seed, oat seed, okra seed, olive seed, onion seed, palm seed, pea seed, peanut seed, pepper seed, poplar seed, pumpkin seed, Radiata pine seed, radish seed, rapeseed seed, rice seed, rye seed, spinach seed, sorghum seed, squash seed, Southern pine seed, soybean seed, strawberry seed, sugarbeet seed, sugarcane seed, sunflower seed, sweet corn seed, sweetgum seed, tea seed, tobacco seed, tomato seed, turf seed, watermelon seed, wheat seed, and *Arabidopsis thaliana* seed. And, crops analyzed using the sampled seeds and/or tissue samples obtained as disclosed herein may include forage crops, oilseed crops, grain crops, fruit crops, ornamental plants, vegetable crops, fiber crops, spice crops, nut crops, turf crops, sugar crops, beverage crops, tuber crops, root crops, forest crops, etc.

In another example embodiment, a seed sampling system includes an automated seed loading assembly operable to singulate seeds from a plurality of seed, an automated seed sampling assembly operable to remove samples (e.g., tissue samples, etc.) from the singulated seeds, and an automated seed transport assembly operable to transfer the singulated seeds from the seed loading assembly to the seed sampling assembly. The seed transport assembly includes multiple retention members, and each of the retention members is movable relative to the seed loading assembly and to the seed sampling assembly. In addition, the seed transport assembly is operable to position one of the multiple retention members adjacent to the seed loading assembly for engaging one of the singulated seeds, while positioning another of the retention members adjacent to the seed sampling assembly for presenting another of the singulated seeds to the seed sampling assembly.

In addition (or alternatively), the seed loading assembly of this embodiment may include at least one elevator unit operable to actuate the singulated seeds into a position to be engaged by one of the multiple retention members of the seed transport assembly. The at least one elevator unit may include a vacuum cup configured to help hold the singulated seeds on the at least one elevator unit. The seed loading assembly may also (or alternatively) include multiple orientation units each configured to orient one of the singulated seeds in a desired orientation. The multiple orientation units may each include an actuator configured to orient one of the singulated seeds and a support configured to receive the oriented seed from the actuator in preparation for transfer to the to the seed sampling assembly. The support may also be operable to sense if the seed is in a desired orientation.

In addition (or alternatively), the seed transport assembly of this embodiment may be operable to position one of the multiple retention members adjacent to the seed loading assembly for engaging one of the singulated seeds while at substantially the same time positioning another of the retention members adjacent to the seed sampling assembly for presenting another of the singulated seeds to the seed sampling assembly. The seed transport assembly may also (or alternatively) include a transport carousel, with each of the multiple retention members mounted to the transport carousel. And, the multiple retention members may include at least four retention members disposed circumferentially about the transport carousel. Also (or alternatively), each of the multiple retention members may include a suction cup for holding one of the singulated seeds. The suction cup of each of the retention members may also (or alternatively) be configured to actuate relative to the transport carousel for positioning singulated seeds adjacent the seed sample assembly.

In addition (or alternatively), the seed sampling assembly of this embodiment may include a sampler for removing a sample from a seed while protecting germination viability of the sampled seeds. The sampler may be configured to orient the seed in a desired position in the sampler prior to removing the sample from said seed. For example, the sampler may include a channel configured to guide the seed into a desired position when one of the multiple retention members actuates to position the seed adjacent the sampler. The channel may be defined by two ramp surfaces configured to direct said seed into the desired position in the sampler. The sampler may include a cutting wheel for removing a sample from a seed. The cutting wheel may be configured to rotate about an off-center axis to thereby remove a progressively deeper sample from the seed as the cutting wheel rotates.

In addition (or alternatively), the seed sampling assembly may include multiple samplers aligned generally linearly along an axis. And, the transport carousel may be operable to rotate about an axis to position one of the retention members adjacent at least one of the multiple samplers. Here, the linear axis of the multiple samplers may be oriented generally parallel to the rotational axis of the transport carousel.

The seed sampling system may be operable to process at least about four seeds per second. In addition (or alternatively), the seed sampler system may be operable with any desired type of seeds (e.g., wheat seeds, corn seeds, cotton seeds, soybean seeds, etc.), and/or may be operable with at least two or more different types of seeds.

In another example embodiment, a seed sampling system includes an automated seed loading assembly having a seed bin and being operable to separate individual seeds from a plurality of seeds within the seed bin, an automated seed transport assembly including a transport carousel and multiple banks of retention members mounted on the transport carousel, and an automated seed sampling assembly including multiple automated samplers linearly disposed along an axis adjacent to the transport carousel, each of the multiple automated samplers operable to remove a sample from a seed. The transport carousel is configured to rotate about an axis to transport the multiple banks of retention members between the samplers and the seed loading assembly. And, the axis of rotation of the transport carousel is substantially parallel to the linear axis defined by the disposition of the samplers.

In addition (or alternatively), the seed loading assembly of this embodiment may include multiple elevator units operable to actuate seeds received from the seed bin into a position to be engaged by the retention members of the seed transport assembly. The elevator units may each include a vacuum cup configured to help hold the seeds on the elevator units. The seed loading system may also (or alternatively) include multiple orientation units configured to orient the separated seeds in a desired orientation. The multiple orientation units may each include an actuator configured to orient one of the singulated seeds and a support configured to receive the oriented seed from the actuator in preparation for transfer to the to the seed sampling assembly. The support may also be operable to sense if the seed is in a desired orientation.

In addition (or alternatively), the seed transport assembly may be operable to position one of the retention members adjacent to the seed loading assembly for engaging one of the separated seeds, while positioning another of the retention members adjacent to one of the samplers of the seed sampling assembly for presenting another of the separated seeds to the sampler. The seed transport assembly may include four banks of retention members substantially uniformly oriented around the transport carousel.

In addition (or alternatively), the seed sampling assembly of this embodiment may include a number of samplers corresponding to a number of retention members included in a bank of the seed transport assembly. For example, the seed sampling assembly may include twelve samplers and each bank of the seed transport assembly may include twelve retention members. The samplers may be configured to orient the seeds in a desired position in the samplers prior to removing the samples from said seeds. For example, the samplers may include channels configured to guide the seeds into desired positions when the retention members actuate to position the seeds adjacent the samplers. The channels may be defined by ramp surfaces configured to direct the seeds into the desired positions in the samplers.

The seed sampling system may be operable to process at least about four seeds per second. In addition (or alternatively), the seed sampler system may be operable with any desired type of seeds (e.g., wheat seeds, corn seeds, cotton seeds, soybean seeds, etc.), and/or may be operable with at least two or more different types of seeds.

In another example embodiment, an automated method for removing samples from seeds includes singulating a seed from a plurality of seeds, engaging the singulated seed with a retention member of an automated seed transport assembly, rotating the seed transport assembly about an axis to move the retention member and singulated seed to a position adjacent a sampler of an automated seed sampling assembly, and removing a sample from the singulated seed at the sampler.

Engaging the singulated seed with the retention member may occur at about the same time a sample is being removed from another singulated seed at the sampler. In addition (or alternatively), engaging the singulated seed with a retention member may include holding the singulated seed on the retention member using a vacuum.

In addition, the method may also (or alternatively) include at least one or more of the following operations: actuating the retention member toward the sampler to present the singulated seed to the sampler; receiving the sample removed from the singulated seed in a sample tray and receiving the singulated seed from which the sample is removed in a seed tray; and orienting the singulated seed in a desired orientation.

Where the method includes orienting the singulated seed in a desired orientation, the operation of removing a sample from the singulated seed may include removing a sample from an oriented seed. In addition (or alternatively), the orienting operation may include rolling the singulated seed along a surface until a desired portion of the seed orients along the surface.

The method may be operable to process at least about four seeds per second. In addition (or alternatively), the method may be operable with any desired type of seeds (e.g., wheat seeds, corn seeds, cotton seeds, soybean seeds, etc.), and/or may be operable with at least two or more different types of seeds.

Seeds and/or tissue samples obtained from the seeds using the seed sampling systems (e.g., system 10, system 110, etc.) and related methods of the present disclosure can be analyzed as desired. For example, the sampled seeds and/or their tissue samples can be analyzed for desired traits of interest (e.g., physical, chemical, morphological, and/or genetic characteristics; markers; genotypes; etc.), etc. Generally, such traits are determined by analyzing the samples for one or more characteristics indicative of at least one genetic or chemical trait. And, analyses may include ones for starch content, protein content, oil content, determination of fatty acid profiles, etc.

Seeds and/or tissue samples obtained from the seeds using the seed sampling systems (e.g., system 10, system 110, etc.) and related methods of the present disclosure can also be used to facilitate germplasm improvement activities. For example, the seeds and/or their tissue samples may be analyzed to identify and select seeds comprising one or more desired traits, markers, and genotypes. In one aspect, analytical methods may be included with the seed sampling systems (e.g., system 10, system 110, etc.) and related methods of the present disclosure to allow individual seeds that are present in a batch or a bulk population of seeds to be analyzed such that the chemical and/or genetic characteristics of the individual seeds can be determined.

Non-limiting examples of traits of interest include color (e.g., white verses red, etc.), size, shape, seed type, resistance to pests (e.g., insects, mites, fungi, yeasts, molds, bacteria, nematodes, weeds, and parasitic and saprophytic plants, etc.), falling number score, baking or noodle quality, etc.

More particularly, non-limiting examples of characteristics indicative of chemical traits include proteins, oils, carbohydrates, fatty acids, amino acids, biopolymers, pharmaceuticals, starch, fermentable starch, secondary compounds, metabolites, etc. Accordingly, non-limiting examples of chemical traits include amino acid content, protein content, protein composition, starch content, fermentation yield, fermentation efficiency, energy yield, oil content, determination of protein profiles determination of fatty acid profiles, determination of metabolite profiles, etc.

And, non-limiting examples of characteristics indicative of genetic traits may include, for example, genetic markers, single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, methylation patterns, etc.

In one embodiment, the seed sampling systems (e.g., system 10, system 110, etc.) and related methods of the present disclosure can be used for removing tissue samples from wheat seeds. The tissue samples can then be analyzed for any desired features (e.g., color (e.g., white verses red, etc.), protein composition, falling number score, baking or noodle quality, etc.). Based on this analysis (e.g., based on presence or absence of one or more desired feature, etc.), sampled wheat seeds can be selected for further use (e.g., further analysis, cultivation, packaging, use in breeding operations, etc.).

In one embodiment, the seed samples obtained using the seed sampling systems (e.g., system 10, system 110, etc.) and related methods include endosperm tissue which enables the determination of allele frequencies, whereby it is possible to infer parental linkage phase for a particular marker. Further, comparison of allele frequency data between two or more germplasm pools provides insight into the targets of selection, whereby alleles increasing in frequency in conjunction with a shift in distribution of one or more traits are presumed to be linked to said trait or traits of interest. Also, evaluation of relative allele frequency data between lines can contribute to the construction of genetic linkage maps.

In another embodiment, the seed samples obtained using the seed sampling systems (e.g., system 10, system 110, etc.) and related methods can be used with doubled haploid technologies to contribute to germplasm improvement activities including economization of doubled haploid programs by selecting only preferred seed for doubling. For example, the seed samples may be taken to include haploid and doubled haploid material and analyzed for both genotypic and chemical characteristics, and then used in connection with trait integration and evaluation and marker-assisted breeding.

Seeds and/or tissue samples obtained from the seeds using the seed sampling systems (e.g., system 10, system 110, etc.) and related methods of the present disclosure can also be used in a breeding program to select plants or seeds having a desired genetic or chemical trait, wherein a desired genetic trait comprises a genotype, a haplotype, an allele, a sequence, a transcript profile, and a methylation pattern. For example, the seeds and/or their tissue samples can be used in combination with any breeding methodology and can be used to select a single generation or to select multiple generations. The choice of breeding method depends on the mode of plant reproduction, the heritability of the trait(s) being improved, and the type of cultivar used commercially (e.g., F1 hybrid cultivar, pureline cultivar, etc). Selected, non-limiting approaches for breeding the plants are set forth below. It is further understood that any commercial and non-commercial cultivars can be utilized in a breeding program. Factors including, for example, without limitation, emergence vigor, vegetative vigor, stress tolerance, disease resistance, branching, flowering, seed set, seed size, seed density, standability, and threshability will generally dictate the choice.

In a particular embodiment, the seeds and/or the tissue samples obtained from the seeds using the seed sampling systems (e.g., system 10, system 110, etc.) and related methods of the present disclosure are used to determine the genetic characteristics of seeds in a marker-assisted breeding program. This allows for improved marker-assisted breeding programs wherein direct seed sampling (such as disclosed herein) can be conducted while maintaining the identity of individual seeds from the seed sampling system (e.g., system 10, system 110, etc.) to the field. As a result, the marker-assisted breeding program results in a "high-throughput" and more efficient platform wherein a population of seeds having a desired trait, marker or genotype can be more effectively bulked in a shorter period of time, with less field and labor resources required. Such advantages will be more fully described below.

In some example embodiments, the seeds and/or the tissue samples obtained from the seeds using the seed sampling systems (e.g., system 10, system 110, etc.) and related methods of the present disclosure can be used in connection with processes for analyzing nucleic acids extracted from the seeds and/or samples for the presence or absence of at least one genetic marker. Desired seeds can then be selected, based on the results of the nucleic acid analysis, for example, for cultivating plants, etc.

For example, DNA may be extracted from the tissue samples using any DNA extraction methods known to those of skill in the art which will provide sufficient DNA yield, DNA quality, PCR response, and sequencing methods response. A non-limiting example of suitable DNA-extraction methods is SDS-based extraction with centrifugation. In addition, the extracted DNA may be amplified after extraction using any amplification method known to those skilled in the art. For example, one suitable amplification method is the GenomiPhi® DNA amplification prep from Amersham Biosciences.

In addition (or alternatively), RNA may be extracted from the tissue samples using any RNA extraction methods known to those of skill in the art which will provide sufficient RNA yield, RNA quality, PCR response, and sequencing methods response. A non-limiting example of suitable RNA-extraction methods is SDS-based extraction with centrifugation with consideration for RNase-free reagents and supplies. In addition, the extracted RNA may be amplified after extraction using any amplification method known to those skilled in the art. For example, one suitable amplification method is the Full Spectrum™ RNA Amplification from System Biosciences.

The extracted nucleic acids are analyzed for the presence or absence of a suitable genetic polymorphism. A wide variety of genetic markers for the analysis of genetic polymorphisms are available and known to those of skill in the art. As used herein, genetic markers include, but are not limited to, simple sequence repeats (SSRs), single nucleotide polymorphisms (SNPs), insertions or deletions (Indels), single feature polymorphisms (SFPs) or transcriptional profiles, and nucleic acid sequences. A nucleic acid analysis for the presence or absence of the genetic marker can be used for the selection of seeds in a breeding population. The analysis may be used to select for genes, QTL, alleles, or genomic regions (haplotypes) that comprise or are linked to a genetic marker. Herein, analysis methods are known in the art and include, but are not limited to, PCR-based detection methods (for example, TaqMan assays), microarray methods, and nucleic acid sequencing methods. The genes, alleles, QTL, or haplotypes to be selected for can be identified using newer techniques of molecular biology with modifications of classical breeding strategies.

In one of these example embodiments, sampled seeds are selected based on the presence or absence of one or more characteristics that are genetically linked with a QTL. Examples of QTLs which are often of interest include but are not limited to herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, or a combination of traits as a multiple trait index. Alternatively, the seeds can be selected based on the presence or absence of one or more characteristics that are genetically linked with a haplotype associated with a QTL. Examples of such QTL may again include without limitation herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, or a combination of traits as a multiple trait index.

Selection of a breeding population could be initiated as early as the F2 breeding level, if homozygous inbred parents are used in the initial breeding cross. An F1 generation could also be sampled and advanced if one or more of the parents of the cross are heterozygous for the alleles or markers of interest. The breeder may analyze an F2 population to retrieve the marker genotype of every individual in the population. Initial population sizes, limited only by the number of available seeds for analysis, can be adjusted to meet the desired probability of successfully identifying the desired number of individuals. Accordingly, the probability of finding the desired genotype, the initial population size, and the targeted resulting population size can be modified for various breeding methodologies and inbreeding level of the sampled population.

The selected seeds may be bulked or kept separate depending on the breeding methodology and target. For example, when a breeder is analyzing an F2 population for disease resistance, all individuals with the desired genotype may be bulked and planted in the breeding nursery. Conversely, if multiple QTL with varying effects for a trait such as grain yield are being selected from a given population, the breeder may keep individual identity preserved, going to the field to differentiate individuals with various combinations of the target QTL.

Several methods of preserving single seed identity can be while transferring sampled seeds from the sampling location (e.g., from the seed sampling system 10, from the seed sample system 110, etc.) to the field. Methods include, but are not limited to, transferring selected individuals (e.g., directly from the seed sampling system 10, the seed sampling system 110, etc.) to trays (e.g., seed tray 80, seed tray 180, etc.), seed tapes, a cassette trays, indexing trays, or transplanting the sampled seeds with peat pots, and hand-planting from individual seed packets.

Multiple cycles of selection can be utilized depending on breeding targets and genetic complexity.

Advantages of using the seed sampling systems (e.g., system 10, system 110, etc.) and related methods of the present disclosure (including the analytic and seed breeding methods) include, without limitation, reduction of labor and field resources required per population or breeding line, increased capacity to evaluate a larger number of breeding populations per field unit, and increased capacity to analyze breeding populations for desired traits prior to planting. Field resources per population are reduced by limiting the field space required to advance the desired genotypes. For example, a population of 1,000 individuals may be planted at 25 seeds per row consuming a total of 40 rows in the field. Using conventional tissue sampling, all 1,000 plants would be tagged and manually sampled by scoring leaf tissue. Molecular marker results would be needed prior to pollination and only those plants containing the desired genetic composition would be pollinated. Thus, if it was determined that 50 seeds contained the desired genetic composition, conventional breeding methodology would have required the planting of 1000 plants to retain the desired 50 seeds. By contrast, the present disclosure allows the breeder to analyze the 1,000 seeds in the lab and select the 50 desired seeds prior to planting. The 50 individuals can then be planted in the field, consuming only two 25 seed rows. Additionally, the present disclosure allows the breed to avoid tagging or sampling in the field, thereby significantly reducing the required manual labor resources.

In addition to reducing the number of field rows per population, using the seed sampling systems (e.g., system 10, system 110, etc.) and related methods of the present disclosure (including the analytic and seed breeding methods) may further allow for increasing the number of populations the breeder can evaluate in a given breeding nursery. Using the above example wherein 50 seeds out of each population of 1000 seeds contained the desired genetic composition, a breeder applying the technology of the present disclosure could evaluate 20 populations of 50 seeds each using the same field area consumed by a single population using conventional field tissue sampling techniques. Even if the populations are selected for a single allele, using a 1:2:1 expected segregation ratio for an F2 population, the breeder could evaluate 4 populations in the same field area as a single field tissue sampled population.

A potential further advantage to using the seed sampling systems (e.g., system 10, system 110, etc.) and related methods of the present disclosure (including the analytic and seed breeding methods) is the mitigation of risks associated with growing plants in certain geographies where plants may grow poorly or experience poor environmental conditions, or may even be destroyed during storms. For example, seeds with the "best" genotype or marker composition could be planted in geography 1 and seeds with the "next best" genotype could be planted in geography 2. In this case geography 2 would be a backup in case any problem befell the plants grown in geography 1. This is very difficult to do with the traditional method of taking tissue samples from germinated plants for genotyping, because these plants would then need to be uprooted and transplanted to the second geography. Using the seed sampling systems (e.g., system 10, system 110, etc.) and related methods of the present disclosure (including the analytic and seed breeding methods) avoids the problem of transplantation and also simplifies the logistics of the breeding program.

In some embodiments, the seed sampling systems (e.g., system 10, system 110, etc.) and related methods of the present disclosure (including the analytic and seed breeding methods) may further be used in a breeding program for introgressing a trait into a plant. Here, nucleic acids extracted from the tissue samples are analyzed for the presence or absence of at least one genetic marker. Seeds are then selected based on the results of the nucleic acids analysis, and plants are cultivated from the selected seeds. The cultivated plants can then be used as either female parents or male parents in crosses with other plants.

Examples of genetic analyses to select seeds for trait integration include, without limitation, identification of high recurrent parent allele frequencies, tracking of transgenes of interest or screening for the absence of unwanted transgenes, selection of hybrid testing seed, selection of seed expressing a gene of interest, selection of seed expressing a heritable phenotype, identification of seed with selected genetic loci, and zygosity testing.

The identification of high recurrent pair allele frequencies using the seed sampling systems (e.g., system 10, system 110, etc.) and related methods of the present disclosure (including the analytic and seed breeding methods) again allows for a reduced number of rows per population and an increased number of populations, or inbred lines, to be planted in a given field unit. Thus, the present disclosure may also effectively reduce the resources required to complete the conversion of inbred lines.

The seed sampling systems (e.g., system 10, system 110, etc.) and related methods of the present disclosure and tissue samples obtained therefrom (and the described analytic and seed breeding methods) further provide quality assurance (QA) and quality control (QC) by assuring that regulated or unwanted transgenes, undesirable genetic traits, or undesirable inherited phenotypes are identified and discarded prior to planting. This application in a QA capacity could effectively eliminate unintentional release infractions. A further extension of the present disclosure is to screen for the presence of infectious agents and remove contaminated seed prior to shipping.

The seed sampling systems (e.g., system 10, system 110, etc.) and related methods of the present disclosure (and the described analytic and seed breeding methods) may be further applied to identify hybrid seed for transgene testing. For example, in a conversion of an inbred line at the BCnF1 stage, a breeder could effectively create a hybrid seed lot (barring gamete selection) that was 50% hemizygous for the trait of interest and 50% homozygous for the lack of the trait in order to generate hybrid seed for testing. The breeder could then analyze all F1 seeds produced in the test cross and identify and select those seeds that were hemizygous. Such method is advantageous in that inferences from the hybrid trials would represent commercial hybrid genetics with regard to trait zygosity.

Other applications of the seed sampling systems (e.g., system 10, system 110, etc.) and related methods of the present disclosure (including the described analytic and seed breeding methods) include use in identifying, tracking, and stacking traits of interest, which carry the same advantages identified above with respect to required field and labor resources. Generally, transgenic conversion programs are executed in multi-season locations which carry a much higher land and management cost structure. As such, the impact of either reducing the row needs per population or increasing the number of populations within a given field unit are significantly more dramatic on a cost basis versus temperate applications.

The seed sampling systems (e.g., system 10, system 110, etc.) and related methods of the present disclosure (including the described analytic and seed breeding methods) may also be used for seeds from plants with two or more transgenes, wherein accumulating or stacking of transgenic regions into plants or lines is achieved by addition of transgenes by transformation, or by crossing parent plants or lines containing different transgenic regions, or any combination of these. Analyses can be conducted to select individual seeds on the basis of the presence of one or more characteristics associated with at least one transgene. Such characteristics include, but are not limited to, a transgene per se, a genetic marker linked to a transgene, mRNA expressed from a transgene, and a protein product of a transgene.

Still further, the seed sampling systems (e.g., system 10, system 110, etc.) and related methods of the present disclosure (including the described analytic and seed breeding methods) may be used to improve the efficiency of the doubled haploid program through selection of desired genotypes at the haploid stage and identification of ploidy level to eliminate non-haploid seeds from being processed and advancing to the field. Both applications again result in the reduction of field resources per population and the capability to evaluate a larger number of populations within a given field unit.

Doubled haploid (DH) plants provide an invaluable tool to plant breeders, particularly for generating inbred lines. A great deal of time is spared as homozygous lines are essentially instantly generated, negating the need for multigenerational conventional inbreeding.

In particular, because DH plants are entirely homozygous, they are very amenable to quantitative genetics studies. Both additive variance and additive x additive genetic variances can be estimated from DH populations. Other applications include identification of epistasis and linkage effects. For breeders, DH populations have been particularly useful in QTL mapping, cytoplasmic conversions, and trait introgression. Moreover, there is value in testing and evaluating homozygous lines for plant breeding programs. All of the genetic variance is among progeny in a breeding cross, which improves selection gain.

However, it is well known in the art that DH production process is inefficient and can be quite labor-intensive. While doubled haploid plants can occur spontaneously in nature, this is extremely rare. Most research and breeding applications rely on artificial methods of DH production. The initial step involves the haploidization of the plant which results in the production of a population comprising haploid seed. Non-homozygous lines are crossed with an inducer parent, resulting in the production of haploid seed. Seed that has a haploid embryo, but normal triploid endosperm, advances to the second stage. That is, haploid seed and plants are any plant with a haploid embryo, independent of the ploidy level of the endosperm.

After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number These chimeric plants are self-pollinated to produce diploid (doubled haploid) seed. This DH seed is cultivated and subsequently evaluated and used in hybrid testcross production.

However, processes for producing DH seed generally suffer from low efficacy even though methods have been developed in an attempt to increase DH production frequency, including treatment with colchicines. Outstanding issues include low production of haploid seed, reduced gamete viability resulting in diminished self-pollination for DH plant generation, and inadequate DH seed yield for breeding applications.

The seed sampling systems (e.g., system 10, system 110, etc.) and related methods of the present disclosure (including the described analytic and seed breeding methods) represent an advance in breeding applications by facilitating the potential for selection at the haploid as well as the diploid seed stage. For example, the seed sampling systems (e.g., system 10, system 110, etc.) and related methods of the present disclosure (including the described analytic and seed breeding methods) can provide for the high-throughput sampling of an entire population of haploid seed, and allow for the subsequent analysis of the samples removed from the seeds. This can also provide for the high-throughput bulking of an entire population of doubled haploid seeds. The samples may be analyzed for the presence or absence of one or more characteristics indicative of at least one genetic or chemical trait and, based on the results of the analysis, one or more individual doubled haploid seeds can then be selected and plants or plant tissue can cultivated from the selected doubled haploid seeds.

The seed sampling systems (e.g., system 10, system 110, etc.) and related methods of the present disclosure (including the described analytic and seed breeding methods) can also include operations associated therewith for analyzing seeds for one or more characteristics, such as, for example, genetic markers, transgenes, markers linked to or diagnostic of transgenes, characteristics related to event performance, event evaluation, and trait integration, etc. to determine whether the seeds are in a haploid or diploid state and/or to select preferred genotypic and phenotypic classes to undergo doubling.

In another embodiment, the seed sampling systems (e.g., system 10, system 110, etc.) and related methods of the present disclosure (including the described analytic and seed breeding methods) can be used with operations for determining linkage phase. By using seed endosperm tissue derived from a diploid plant, the parental marker haplotypes can be determined using a genotyping system that enables detection of different allele frequencies in DNA samples. Since endosperm tissue is triploid, with two copies derived from the female gamete, the linkage phase of the parental line can be derived by dissecting heterozygous progeny genotypes (see FIG. 1). The DNA sample from endosperm tissue allows for a determination of the ploidy level of the genetic marker. A diploid ploidy level in the genetic marker indicates maternal inheritance and a haploid ploidy level in the genetic marker indicates paternal inheritance.

Further, differential allele frequency data can be used to infer the genetic linkage map but, unlike methods requiring haploid material, using the above-described allele frequency calling. Determination of the genetic linkage map has tremendous utility in the context of haplotype characterization, mapping of marker (or haplotype)—trait associations. This is particularly robust on a single, vs. bulked, seed basis and is thus well-suited for use in association with the seed sampling systems (e.g., system 10, system 110, etc.) and related methods of the present disclosure (including the described analytic and seed breeding methods).

In another embodiment, the seed sampling systems (e.g., system 10, system 110, etc.) and related methods of the present disclosure (including the described analytic and seed breeding methods) may further be used in connection with an assay for predicting embryo zygosity for a particular gene of interest (GOI). The assay predicts embryo zygosity based on the ratio of the relative copy numbers of a GOI and of an internal control (IC) gene per cell or per genome. Generally, this assay uses an IC gene that is of known zygosity, e.g., homozygous at the locus (two IC copies per diploid cell), for normalizing measurement of the GOI. The ratio of the relative copy numbers of the IC to the GOI predicts the GOI copy number in the cell. In a homozygous cell, for any given gene (or unique genetic sequence), the gene copy number is equal to the cell's ploidy level since the sequence is present at the same locus in all homologous chromosomes. When a cell is heterozygous for a particular gene (or hemizygous in the case of a transgene), the gene copy number will be lower than the cell's ploidy level. If the GOI is not detected, the cell is null for the locus, as can happen for a negative segregant of a transgenic event or in a mutagenized population. The zygosity of a cell at any locus can thus be determined by the gene copy number in the cell.

In a particular embodiment, the seed sampling systems (e.g., system 10, system 110, etc.) and related methods of the present disclosure (including the described analytic and seed breeding methods) may be used in connection with an assay for predicting corn embryo zygosity. In corn seed, the endosperm tissue is triploid, whereas the embryo tissue is diploid. Endosperm copy number is reflective of the zygosity of the embryo: a homozygous (positive or negative) endosperm accompanies a homozygous embryo, heterozygous endosperm (whether a GOI copy number of 1 or 2) reflects a heterozygous (GOI copy number of 1) embryo. Endosperm that is homozygous for the IC will contain three IC copies. Endosperm GOI copy number can range from 0 (homozygous negative embryo) to 3 (homozygous positive embryo); and endosperm GOI copy number of 1 or 2 is found in seed where the embryo is heterozygous for the GOI (or hemizygous for the GOI if the GOI is a transgene). The endosperm GOI copy number (which can range from 0 to 3 copies) can be determined from the ratio of endosperm IC copy number to endosperm GOI copy number (which can range from 0/3 to 3/3, that is, from 0 to 1), which can then be used to predict zygosity of the embryo.

Copy numbers of the GOI or of the IC can be determined by any convenient assay technique for quantification of copy numbers, as is known in the art. Examples of suitable assays include, but are not limited to, Real Time (TaqMan®) PCR (Applied Biosystems, Foster City, Calif.) and Invader® (Third Wave Technologies, Madison, Wis.) assays. Preferably, such assays are developed in such a way that the amplification efficiency of both the IC and GOI sequences are equal or very similar. For example, in a Real Time TaqMan® PCR assay, the signal from a single-copy GOI (the source cell is determined to be heterozygous for the GOI) will be detected one amplification cycle later than the signal from a two-copy IC, because the amount of the GOI is half that of the IC. For the same heterozygous sample, an Invader® assay would measure a GOI/IC ratio of about 1:2 or 0.5. For a sample that is homozygous for both the GOI and the IC, the GOI signal would be detected at the same time as the IC signal (TaqMan®), and the Invader assay would measure a GOI/IC ratio of about 2:2 or 1.

These guidelines apply to any polyploid cell, or to haploid cells (such as pollen cells), since the copy number of the GOI or of the IC remain proportional to the genome copy number (or ploidy level) of the cell. Thus, these zygosity assays can be performed on triploid tissues such as corn endosperm. Furthermore, the copy number for a GOI can be measured beyond 2 copies or at numerically different values than the ploidy of the cell. The method is still appropriate for detecting GOI in polyploids, in some transgenic events with >2 copies of the inserted transgene, after replication of the GOI by transposition, when the GOI exists on autonomously replicating chromosomes or plasmids and other situations.

In plant breeding, it is useful to determine zygosity at one or more loci for the purpose of evaluating the level of inbreeding (that is, the degree of gene fixation), segregation distortion (i.e., in transgenic germplasm, maternal inheritance testing or for loci that affect the fitness of gametes), and the level of outbreeding (i.e., the relative proportion of homozygosity and heterozygosity). Similarly, the extent of zygosity at one or more loci can be used to estimate hybridity and whether a particular seed lot meets a commercial or regulatory standard for sale as certified hybrid seed. In addition, in transgenic germplasm, it is useful to know the ploidy, or copy number, in order to distinguish between quality events and to aid in trait integration strategies.

In another embodiment, the seed sampling systems (e.g., system 10, system 110, etc.) and related methods of the present disclosure (including the described analytic and seed breeding methods) may be used in connection with operations for improving the ability to monitor one or more germplasm pools for shifts in the frequencies of one or more genetic characteristics, wherein said genetic characteristics include markers, alleles, and haplotypes. Methodology is known in the art to compare genetic marker frequency between recently derived populations and their ancestral lines in order to identify those genetic loci that are increasing in frequency over time (U.S. Pat. Nos. 5,437,697 and 5,746,023). Those loci with frequencies that exceed the expected allele frequency are inferred to have been subject to selection. Further, given that the predominant selection criterion in breeding programs is yield, it is expected that those increasingly frequent alleles may be linked to yield.

In a particular embodiment, the seed sampling systems (e.g., system 10, system 110, etc.) and related methods of the present disclosure (including the described analytic and seed breeding methods) may be used in connection with operations to enable haplotype-assisted breeding. By comparing the frequency of haplotypes in emerging elite lines with the haplotype frequency in the ancestral elite lines (as determined via pedigree analysis), identification of haplotypes that are deviating from the expected haplotype frequency is possible. Further, by evaluation of haplotype effect estimates for said haplotypes, it is also possible to link said haplotypes of increasing frequency with phenotypic outcomes for a suite of agronomic traits. The haplotype composition of individual seeds sampled from a plurality of seeds can be determined using genetic markers and the seeds with preferred haplotypes are selected and advanced. Thus, more informed breeding decisions and establishment of superior line development programs is enabled by this technology.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Example embodiments have been provided so that this disclosure will be thorough, and will fully convey the scope to those who are skilled in the art. Numerous specific details are set forth such as examples of specific components, assemblies, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, components, and/or groups thereof, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, seeds, members and/or sections, these elements, components, seeds, members and/or sections should not be limited by these terms. These terms may be only used to distinguish one element, component, seed, member or section from another element, component, seed, member or section. Terms such as "first," "second," and other numerical terms when used herein do not imply a sequence or order unless clearly indicated by the context. Thus, a first element, component, seed, member or section discussed below could be termed a second element, component, seed, member or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A seed sampling system, comprising:
   an automated seed loading assembly operable to singulate seeds from a plurality of seeds;
   samplers configured to receive the singulated seeds and remove tissue samples from the seeds; and
   an automated seed transport assembly having multiple retention members configured to transfer the singulated seeds from the seed loading assembly to the samplers, the seed transport assembly operable to position one of the retention members adjacent the seed loading assembly for engaging a singulated seed while positioning another of the retention members adjacent to at least one of the samplers for presenting another singulated seed to the at least one of the samplers;
   wherein the at least one of the samplers is configured to engage the presented seed, prior to removing a tissue sample from said seed, and orient said seed in a desired position while said seed is held by the another one of the retention members.

2. The system of claim 1, wherein the at least one of the samplers is further configured to remove the tissue sample from the presented seed while maintaining germination viability of said seed.

3. The system of claim 2, wherein the at least one of the samplers includes a channel defined by two ramp surfaces configured to direct the presented seed into the desired position in said sampler.

4. The system of claim 2, wherein the at least one of the samplers includes a cutting device configured to remove the tissue sample from the presented seed.

5. The system of claim 1, wherein said another of the retention members is adjustable to allow the at least one of the samplers to orient the presented seed while the seed is held by said another of the retention members.

6. A seed sampling system, comprising:
   an automated seed loading assembly operable to singulate seeds from a plurality of seeds, the seed loading assembly including multiple orientation units disposed along a first axis, each of the orientation units configured to orient one of the singulated seeds in a desired position;
   an automated seed sampling assembly having multiple samplers disposed along a second axis generally parallel to the first axis, each of the multiple samplers configured to remove a tissue sample from one of the oriented seeds; and
   an automated seed transport assembly operable to receive the oriented seeds from the orientation units of the seed loading assembly and transfer the oriented seeds from the orientation units to the samplers of the seed sampling assembly, the automated seed transport assembly configured to rotate about an axis generally parallel to the first axis and the second axis to transfer the oriented seeds from the orientation units to the samplers.

7. The system of claim 6, wherein each of the multiple orientation units includes an actuator configured to orient one of the singulated seeds and a support configured to receive the oriented seed from the actuator in preparation for transfer to the samplers of the seed sampling assembly.

8. The system of claim 7, wherein the support is operable to sense if the seed is in a desired orientation.

9. The system of claim 7, wherein each of the multiple orientation units includes a guide surface; and
   wherein, for each of the multiple orientation units, the actuator is configured to move the one of the singulated seeds along the guide surface to thereby orient the one of the singulated seeds.

10. The system of claim 6, wherein the seeds are wheat seeds.

11. The system of claim 6, wherein the automated seed transport assembly includes multiple retention members, each of the retention members configured to receive one of the oriented seeds from one of the orientation units of the seed loading assembly and transfer the received oriented seed to a corresponding one of the samplers of the seed sampling assembly.

12. The system of claim 6, wherein the seed loading assembly further includes sensors configured to sense the singulated seeds in the orientation units.

13. An automated method for removing tissue samples from seeds, the method comprising:

receiving individual seeds in multiple orientation units of an automated seed loading assembly, the orientation units disposed along a first axis;

orienting the individual seeds in the orientation units at about the same time;

after the individual seeds are oriented, receiving each of the oriented seeds in an automated seed transport assembly and transferring each of the oriented seeds, by the seed transport assembly, from the orientation units to a corresponding one of multiple samplers of an automated seed sampling assembly disposed along a second axis generally parallel to the first axis, by rotating about an axis generally parallel to the first axis and the second axis; and removing tissue samples from the transferred seeds at the samplers.

14. The method of claim 13, further comprising receiving the tissue samples removed from the seeds in a sample tray, and receiving the seeds from which the tissue samples are removed in a seed tray.

15. The method of claim 13, further comprising:

analyzing the tissue samples for one or more characteristics selected from the group consisting of a genetic marker, a single nucleotide polymorphism, a simple sequence repeat, a restriction fragment length polymorphism, a haplotype, a tag SNP, an alleles of a genetic marker, a gene, a DNA-derived sequence, an RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern; and/or analyzing the tissue samples and either selecting or not selecting the seeds from which the tissue samples are removed based on the presence of one or more characteristics in the tissue sample that are genetically linked with a QTL selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, traits for improved consumer appeal, and a combination of traits as a multiple trait index; and/or analyzing the tissue samples and either selecting or not selecting the seeds from which the tissue samples are removed based on the presence of one or more characteristics in the tissue sample that are genetically linked with a haplotype associated with a QTL selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, traits for improved consumer appeal, and a combination of traits as a multiple trait index.

16. The method of claim 13, wherein transferring each of the oriented seeds from the orientation units to a corresponding one of multiple samplers of an automated seed sampling assembly includes transferring each of the oriented seeds with one of multiple retention members of the automated seed transport assembly; and further comprising actuating the retention members toward the samplers of the automated seed sampling assembly to present the oriented seeds to the samplers so that the samplers can remove the tissue samples from the seeds.

17. The method of claim 13, wherein orienting the individual seeds in the orientation units includes moving the individual seeds, via actuators, along guide surfaces of the orientation units.

* * * * *